(12) United States Patent
Ueda et al.

(10) Patent No.: US 7,195,600 B2
(45) Date of Patent: Mar. 27, 2007

(54) BIOLOGICAL DATA MEASUREMENT SYSTEM FOR PREGNANT WOMEN

(75) Inventors: Yasuo Ueda, Sasayama (JP);
Motoyoshi Maruo, Sarda (JP);
Yoshihiko Ashitaka, Ashiya (JP);
Tomoko Takehara, Tokyo (JP); Yuka Honda, Tokyo (JP)

(73) Assignee: Tanita Corporation, Tokyo (JP)

( * ) Notice: Subject to any disclaimer, the term of this patent is extended or adjusted under 35 U.S.C. 154(b) by 0 days.

(21) Appl. No.: 11/388,971

(22) Filed: Mar. 27, 2006

(65) Prior Publication Data
US 2006/0217630 A1 Sep. 28, 2006

(30) Foreign Application Priority Data
Mar. 28, 2005 (JP) .............................. 2005-090527

(51) Int. Cl.
*A61B 10/00* (2006.01)
*A61B 5/05* (2006.01)

(52) U.S. Cl. ...................... 600/551; 600/547
(58) Field of Classification Search ................ 600/551, 600/547, 587, 591, 300
See application file for complete search history.

(56) References Cited

U.S. PATENT DOCUMENTS

| | | | |
|---|---|---|---|
| 4,951,197 A | 8/1990 | Mellinger | |
| 6,369,338 B1* | 4/2002 | Kimura | 177/25.16 |
| 2004/0243020 A1* | 12/2004 | Ueda et al. | 600/547 |
| 2005/0020888 A1* | 1/2005 | Harima et al. | 600/300 |
| 2005/0085742 A1* | 4/2005 | Ueda et al. | 600/547 |
| 2006/0167373 A1* | 7/2006 | Takehara et al. | 600/547 |

FOREIGN PATENT DOCUMENTS

| | | |
|---|---|---|
| EP | 1 080 687 | 3/2001 |
| EP | 1 195 138 | 4/2002 |
| EP | 1 279 367 | 1/2003 |
| EP | 1 481 634 | 12/2004 |
| EP | 1 491 140 | 12/2004 |
| EP | 1 508 297 | 2/2005 |
| JP | 62-169023 | 7/1987 |
| JP | 07-100122 | 4/1995 |
| JP | 2002-112982 | 4/2002 |

(Continued)

OTHER PUBLICATIONS

Ishikawa, H. (Publisher), "Dietary Reference Intakes for Japanese People, 6th Revision, Minister for Health and Welfare- Japan" 1st Edition Sep. 1999, pp. 35-39.

(Continued)

*Primary Examiner*—Max F. Hindenburg
*Assistant Examiner*—H. Q. Nguyen
(74) *Attorney, Agent, or Firm*—McDermott Will & Emery LLP

(57) ABSTRACT

Disclosed is a maternity biodata measurement system, wherein a sum of a pre-pregnancy energy expenditure and a pregnancy extra energy amount of a subject is determined as an energy amount necessary for the subject in a pregnancy period. In particular, the pregnancy extra energy amount is determined based on pre-pregnancy body-mass index data and elapsed pregnancy-period data about the subject, so as to allow the necessary energy amount to be determined as a value appropriate for the subject. The maternity biodata measurement system of the present invention makes it possible to measure a necessary energy amount for a pregnant woman on an individual basis.

43 Claims, 13 Drawing Sheets

FOREIGN PATENT DOCUMENTS

| JP | 2002-172099 | 6/2002 |
|---|---|---|
| JP | 2003-102696 | 4/2003 |
| JP | 2004-351053 | 12/2004 |
| JP | 2005-014664 | 1/2005 |
| JP | 2005-137885 | 6/2005 |

OTHER PUBLICATIONS

Mochizuki, M., "Pregnancy & Variations in Water/Electrolyte and Nutrients" Perinatal Medicine, 1992, vol. 22, pp. 36-44.

Durnin, J. "Energy Requirements of Pregnancy: An Integration of the Longitudinal Data From the Five-Country Study" The Lancet, Nov. 1987, pp. 1131-1133.

Butte, et al., "Energy requirements during pregnancy based on total energy expenditure and energy deposition[1-4]," American Journal of Cliincal Nutrition, Jun. 2004, pp. 1078-1087, vol. 79, No. 6, American Society for Clinical Nutrition, USA.

Van Raaij, "Energy requirements of pregnancy in the Netherlands," Lancet, Oct. 24, 1987, pp. 953-955, vol. 2, No. 8565, Medline.

Extended European Search Report issued in corresponding European Patent Application No. EP 06 00 6395, dated Nov. 28, 2006.

* cited by examiner

FIG. 9

| | |
|---|---|
| MEASUREMENT DATE/TIME | NOVEMBER 9, 2004   10:27 A.M. |
| STATUS | MATERNITY |
| N-TH WEEK OF PREGNANCY | 24TH WEEK AND 5 DAYS |
| AGE | 35 YEARS OLD |
| BODY HEIGHT | 159 cm |
| BODY WEIGHT | 52.4 kg |
| CLOTH WEIGHT | 0.5 kg |
| FETUS WEIGHT | 1.201 kg |
| AMNIOTIC FLUID WEIGHT | 0.534 kg |
| PLACENTA WEIGHT | 0.265 kg |
| IMPEDANCE | 580 Ω |
| BODY FAT PERCENTAGE | 27.5 % |
| FAT MASS | 14.4 kg |
| FAT-FREE MASS | 38.0 kg |
| BODY WATER MASS | 27.8 kg |
| PRE-PREGNANCY BODY WEIGHT | 48.0 kg |
| PRE-PREGNANCY BMI | 19.0 |
| BODY-WEIGHT INCREMENT | 4.4 kg |
| BODY-FAT INCREMENT | 2.0 kg |
| BASAL METABOLISM | 1313 kcal/day |
| BASAL METABOLISM INCREMENT | 150 kcal/day |
| PREGNANCY NECESSARY ENERGY AMOUNT | 1722 kcal/day |
| PREGNANCY EXTRA ENERGY AMOUNT | 210 kcal/day |
| PREGNANCY INTAKE ENERGY AMOUNT | 1970 kcal/day |
| CALORIE EXCESS/DEFICIENCY | + 284 kcal/day |

COMMENT: ABOUT ONE-HALF CUP OF RICE IS TAKEN AS EXCESS CALORIES

EXTRA ENERGY AMOUNT
= an × (N-TH WEEK OF PREGNANCY)$^2$ + bn × N-TH WEEK OF PREGNANCY + cn

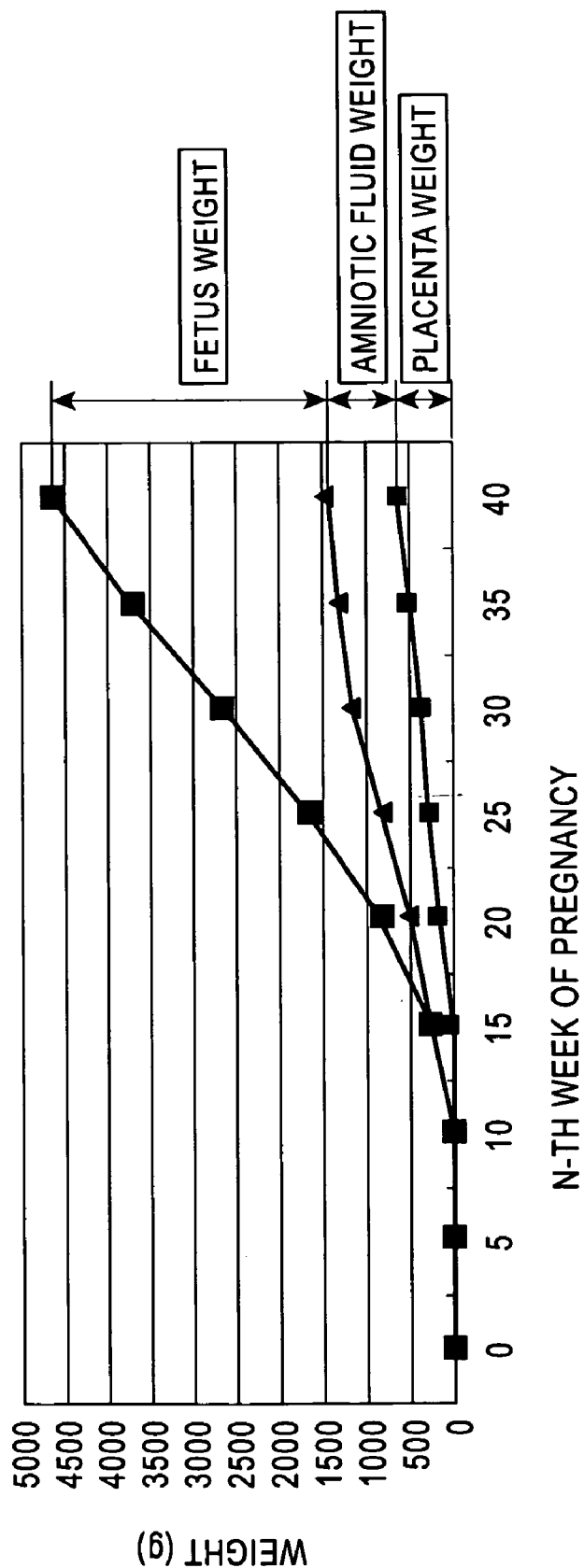

BIOLOGICAL DATA MEASUREMENT SYSTEM FOR PREGNANT WOMEN

TECHNICAL FIELD

The present invention relates to a maternity biodata measurement system for measuring biological data (biodata) about a pregnant woman, and more particularly to a system for measuring an energy amount necessary per day for a pregnant woman and an actually expended energy amount.

BACKGROUND ART

Heretofore, an energy amount necessary per day for a pregnant woman has been estimated based on standard basal metabolism values, daily activity intensities and an extra energy amount (350 kcal) for a pregnant woman, presented by the Ministry of Health, Labor and Welfare, Japan, as disclosed, for example, in the following Non-Patent Publication 1. Specifically, the standard basal metabolism value corresponding to an age of a specific pregnant woman is multiply by a body weight of the pregnant woman to obtain a basal metabolism of the pregnant woman. Then, the obtained basal metabolism is multiply by the daily activity intensity of the pregnant woman, and 350 kcal is added thereto to determine an energy amount necessary per day for the pregnant woman. An energy amount which has been actually expended (taken) in the day by the pregnant woman is estimated by inquiring about the amount and content of food which has been actually taken by the pregnant woman.

As to an energy amount necessary for a pregnant woman, data about energy amount necessary for tissues increased associated with pregnancy, such as protein and fat increased in a fetus, the placenta and the maternal body, and data about increment in basal metabolism associated with hypermetabolism during pregnancy, are disclosed, for example, in the following Non-Patent Publications 2 and 3.

In order to contribute to maternal healthcare, the applicant promotes research and development on technologies for acquiring various biodata of a pregnant woman. As the result of such researches, it was verified that each of a body weight of a fetus, a weight of amniotic fluid and a weight of placenta can be estimated approximately uniquely based on respective elapsed periods from pregnancy (the number of weeks of pregnancy), and variations in fat mass and body water content of a woman measured in a period from her unpregnant state to her current pregnant state are equivalent, respectively, to about 58% and about 29% of an increment in body weight of the woman in the period. The applicant filed patent applications for a maternal body-composition measurement apparatus and a maternal healthcare apparatus utilizing and applying these achievements, as disclosed, for example, in the following Patent Publications 1 to 3.

Further, the applicant recently found a method of estimating a basal metabolism value of a pregnant woman using data, such as a maternal fat-free mass and an age of the pregnant woman, as a parameter, in a simple and easy manner, and filed a patent application for a maternal basal-metabolism measurement apparatus, as disclosed, for example, in the following Patent Publication 4.

The maternity biodata measurement apparatuses as disclosed in the Patent Publications 1 to 4 have already been partly put into practical use, based on body-fat and body-composition analyzers utilizing a so-called bioelectrical impedance analysis, as disclosed, for example, the following Patent Publications 5 and 6, and a method and apparatus for calculating basal metabolism based on a fat-free mass and an age of a subject, as disclosed, for example, the following Patent Publications 7 and 8, or in the form of being incorporated thereinto.

[Non-Patent Publication 1] the Society for Research of Health and Nutrition, "Recommended Dietary Allowance, Dietary Reference Intakes for Japanese People—6th Revision", Dai-Ichi Shuppan Publishing Co. Ltd., Sep. 10, 1999, pp. 35 to 39

[Non-Patent Publication 2] M. MOCHIZUKI and M. OHOHASHI, "Pregnancy & Variations in Water/Electrolyte and Nutrients", Perinatal Medicine, Japan, Tokyoigakusha Co. Ltd., 1992, Vol. 22, Extra No., pp. 36 to 44

[Non-Patent Publication 3] J. V. G. A. DURNIN, "ENERGY REQUIREMENT OF PREGNANCY: AN INTEGRATION OF THE LONGITUDINAL DATA FROM THE FIVE-COUNTRY STUDY", THE LANCET, USA, Nov. 14, 1987, pp. 1131 to 1133

[Patent Publication 1] Japanese Patent Laid-Open Publication No. 2003-102696

[Patent Publication 2] Japanese Patent Laid-Open Publication No. 2004-351053

[Patent Publication 3] Japanese Patent Application No. 2004-218848

[Patent Publication 4] Japanese Patent Application No. 2005-014664

[Patent Publication 5] Japanese Patent Publication No. 05-049050

[Patent Publication 6] Japanese Patent No. 2835662

[Patent Publication 7] Japanese Patent Laid-Open Publication No. 2002-112982

[Patent Publication 8] Japanese Patent Laid-Open Publication No. 2002-172099

DISCLOSURE OF THE INVENTION

As to an energy amount necessary for a pregnant woman, when a necessary energy amount is estimated using the standard basal metabolism values presented by the Ministry of Health, Labor and Welfare, an extra energy amount for a pregnant woman is a constant value of 350 kcal, and any personal parameter, such as physique type, body weight or basal metabolism, is not taken into consideration. Thus, it is difficult to calculate a necessary energy amount suitable for each individual.

Further, as to an intake energy amount of a pregnant woman, it is far from easy in daily life to inquire into the amount and content of actual food intake, and such an inquiry is burdensome to the pregnant woman herself.

While the various types of maternity biodata measurement apparatuses developed by the applicant can measure various biodata of a pregnant woman, such as body weight, fat mass, fat-free mass, body water content and basal metabolism, they are still not sufficient to accurately measure a necessary energy amount and an intake energy amount on an individual basis, and therefore need to be improved in this respect.

Even though an adequate nutritional management depending on an elapsed number of pregnancy weeks (n-th week of pregnancy) and changes in body composition is important for most pregnant women in view of fetal growth and lower physical load during childbirth, they have not been able to learn a necessary energy amount suitable for each individual and a their own actual intake energy amount in a simple and easy manner. As a result, some pregnant women needlessly try to lose weight or reversely tend to overeat. Thus, in view of nutritional management and healthcare for pregnant women, there is the need for providing an apparatus and system capable of measuring a necessary energy amount for a pregnant woman and an intake energy amount of the pregnant woman on an individual basis.

It is a first primary object of the present invention to provide a maternity biodata measurement system capable of measuring a necessary energy amount for a pregnant woman on an individual basis.

It is a second primary object of the present invention to provide a maternity biodata measurement system capable of measuring an intake energy amount of a pregnant woman on an individual basis.

It is yet another object of the present invention to allow a necessary energy amount for a pregnant woman and/or an intake energy amount of the pregnant woman to be measured on an individual basis in a simple and easy manner. Eventually, it is an object of the present invention to allow excess and deficiency in intake energy amount of a pregnant woman to be measured on an individual basis in a simple and easy manner.

In order to achieve the above objects, according to a first aspect of the present invention, there is provided a maternity biodata measurement system for measuring biodata of a pregnant woman who is a subject, which comprises, pre-pregnancy energy-expenditure determination means for determining an energy expenditure of the subject in a pre-pregnancy state, pregnancy extra-energy-amount determination means for determining a suitable extra energy expenditure to be added to the pre-pregnancy energy expenditure due to pregnancy, and pregnancy necessary-energy-amount determination means for determining a sum of the pre-pregnancy energy expenditure and the pregnancy extra energy amount, as an energy amount necessary for the subject in a pregnancy period. The pregnancy extra-energy-amount determination means includes pre-pregnancy body-mass-index data acquisition means for acquiring data about body-mass index of the subject in the pre-pregnancy state, elapsed-pregnancy-period data acquisition means for acquiring data about elapsed period from the pregnancy of the subject, and pregnancy extra-energy-amount estimation means for estimating the pregnancy extra energy amount based on the pre-pregnancy body-mass index data and the elapsed pregnancy-period data.

In the maternity biodata measurement system set forth in the first aspect of the present invention, it is preferable that the pregnancy extra-energy-amount estimation means includes estimation-equation storage means for storing a plurality of estimation equations for calculating the pregnancy extra energy amount using elapsed pregnancy-period data as a parameter, in association with pre-pregnancy body-mass index data, estimation-equation selection means for selecting one of the estimation equations corresponding to the acquired pre-pregnancy body-mass index data, and estimation-equation execution means for assigning the acquired elapsed pregnancy-period data to the selected estimation equation to calculate the pregnancy extra energy amount.

In the maternity biodata measurement system of the present invention, it is preferable that the pre-pregnancy energy-expenditure determination means includes pre-pregnancy basal-metabolism data acquisition means for acquiring data about basal metabolism of the subject in the pre-pregnancy state, daily-activity-intensity data acquisition means for acquiring data about daily activity intensity of the subject, and pre-pregnancy energy-expenditure estimation means for estimating the pre-pregnancy energy expenditure based on the pre-pregnancy basal metabolism data and the daily activity intensity data.

Preferably, the pre-pregnancy basal-metabolism data acquisition means includes pre-pregnancy age data acquisition means for acquiring data about age of the subject in the pre-pregnancy state, pre-pregnancy fat-free-mass data acquisition means for acquiring data about fat-free mass of the subject in the pre-pregnancy state, and pre-pregnancy basal-metabolism data calculation means for calculating the pre-pregnancy basal metabolism data based on the pre-pregnancy age data and the pre-pregnancy fat-free mass data.

Preferably, the pre-pregnancy fat-free-mass data acquisition means includes pre-pregnancy body-weight data acquisition means for acquiring data about body weight of the subject in the pre-pregnancy state, pre-pregnancy fat-mass data acquisition means for acquiring data about fat mass of the subject in the pre-pregnancy state, and pre-pregnancy fat-fee-mass calculation means for calculating the pre-pregnancy fat-free mass data based on the pre-pregnancy body weight data and the pre-pregnancy fat mass data.

Preferably, the pre-pregnancy fat-mass data acquisition means includes maternal fat-mass data acquisition means for acquiring data about maternal fat mass of the subject, body-fat-increment data acquisition means for acquiring data about body-fat increment of the subject in the pregnancy period, and pre-pregnancy fat-mass data calculation means for calculating the pre-pregnancy fat mass data based on the maternal fat mass data and the body-fat increment data.

Preferably, the maternal fat-mass data acquisition means includes body-weight data acquisition means for acquiring data about current body weight of the subject, fetal-region-weight data acquisition means for acquiring data about fetal-region weight in the subject, maternal-weight data calculation means for calculating data about maternal weight of the subject based on the current body weight data and the fetal-region weight data, body-height data acquisition means for acquiring data about body height of the subject, impedance data acquisition means for acquiring data about body impedance of the subject, and maternal fat-mass data calculation means for calculating the maternal fat mass data based on the maternal weight data, the body height data and the impedance data.

Preferably, the fetal-region-weight data acquisition means includes fetal-region-weight data determination means for determining the fetal-region weight data based on the elapsed pregnancy-period data acquired by the elapsed-pregnancy-period data acquisition means.

Preferably, the body-fat-increment data acquisition means includes body-weight-increment data acquisition means for acquiring data about body-weight increment of the subject in the pregnancy period, and body-fat-increment data determination means for determining a value obtained by multiplying the body-weight increment data by a predetermined rate, as the body-fat increment data.

Preferably, the body-weight-increment data acquisition means includes body-weight data acquisition means for acquiring data about current body weight of the subject, and body-weight-increment data calculation means for calculating the body-weight increment data based on the current body weight data and the pre-pregnancy body weight data acquired by the pre-pregnancy body-weight data acquisition means.

Preferably, the maternity biodata measurement system set forth in the first aspect of the present invention further includes pregnancy intake energy amount determination means for determining an energy amount which is actually taken by the subject in the pregnancy period, and intake-energy excess/deficiency data output means for outputting data about excess and deficiency in intake energy amount of the subject based on the pregnancy intake energy amount and the pregnancy necessary energy amount determined by the pregnancy necessary-energy-amount determination means.

Preferably, the maternity biodata measurement system set forth in the first aspect of the present invention further includes basal-metabolism-increment determination means for determining an increment of basal metabolism of the subject in the pregnancy period, increased-tissue-required energy-amount determination means for determining an energy amount required for increased tissue of the subject due to the pregnancy, pregnancy intake-energy-amount determination means for determining a sum of the increment of basal metabolism, the increased-tissue-required energy amount, and the pre-pregnancy energy-expenditure determined by the pre-pregnancy energy-expenditure determination means, as an energy amount which is actually taken by the subject in the pregnancy period, and intake-energy excess/deficiency data output means for outputting data about excess and deficiency in intake energy amount of the subject based on the pregnancy intake energy amount and the pregnancy necessary energy amount determined by the pregnancy necessary-energy-amount determination means. The increased-tissue-required energy-amount determination means includes the elapsed-pregnancy-period data acquisition means, body-fat-increment data acquisition means for acquiring data about body-fat increment of the subject in the pregnancy period, and increased-tissue-required energy-amount estimation means for estimating the increased-tissue-required energy amount based on the elapsed pregnancy-period data and the body-fat increment data.

Preferably, the maternity biodata measurement system set forth in the first aspect of the present invention further includes basal-metabolism data acquisition means for acquiring data about current basal metabolism of the subject, daily-activity-intensity data acquisition means for acquiring data about daily activity intensity of the subject, increased-fat-tissue-required energy-amount determination means for determining an energy amount required for increased maternal fat-tissue of the subject due to the pregnancy, pregnancy intake-energy-amount determination means for determining an energy amount which is actually taken by the subject in the pregnancy period, based on the basal metabolism data, the daily activity intensity data, and the increased-fat-tissue-required energy amount, and intake-energy excess/deficiency data output means for outputting data about excess and deficiency in intake energy amount of the subject based on the pregnancy intake energy amount and the pregnancy necessary energy amount determined by the pregnancy necessary-energy-amount determination means. The increased-fat-tissue-required energy-amount determination means includes the elapsed-pregnancy-period data acquisition means, body-fat-increment data acquisition means for acquiring data about body-fat increment of the subject in the pregnancy period, and increased-tissue-required energy-amount estimation means for estimating the increased-tissue-required energy amount based on the elapsed pregnancy-period data and the body-fat increment data.

According to a second aspect of the present invention, there is provided a maternity biodata measurement system for measuring biodata of a pregnant woman who is a subject, which comprises pre-pregnancy energy-expenditure determination means for determining an energy expenditure of the subject in a pre-pregnancy state, basal-metabolism-increment determination means for determining an increment of basal metabolism of the subject in the pregnancy period, increased-tissue-required energy-amount determination means for determining an energy amount required for increased tissue of the subject due to the pregnancy, pregnancy intake-energy-amount determination means for determining a sum of the pre-pregnancy energy expenditure, the increment of basal metabolism, and the increased-tissue-required energy amount, as an energy amount which is actually taken by the subject in the pregnancy period. The increased-tissue-required energy-amount determination means includes elapsed-pregnancy-period data acquisition means for acquiring data about elapsed period from the pregnancy of the subject, body-fat-increment data acquisition means for acquiring data about body-fat increment of the subject in the pregnancy period, and increased-tissue-required energy-amount estimation means for estimating the increased-tissue-required energy amount based on the elapsed pregnancy-period data and the body-fat increment data.

In the maternity biodata measurement system set forth in the second aspect of the present invention, it is preferable that the increased-tissue-required energy-amount estimation means includes first estimation-equation storage means for storing an estimation equations for calculating first energy amount data using elapsed pregnancy-period data as a parameter, first estimation-equation execution means for assigning the acquired elapsed pregnancy-period data to the first estimation equation to calculate the first energy amount data, second estimation-equation storage means for storing an estimation equations for calculating second energy amount data using body-fat increment data as a parameter, second estimation-equation execution means for assigning the acquired body-fat increment data to the second estimation equation to calculate the second energy amount data, and increased-tissue-required energy-amount calculation means for calculating the increased-tissue-required energy amount based on the acquired elapsed pregnancy-period data and a sum of the first energy amount data and the second energy amount data.

Preferably, the body-fat-increment data acquisition means includes body-weight-increment data acquisition means for acquiring data about body-weight increment of the subject in the pregnancy period, and body-fat-increment data determination means for determining a value obtained by multiplying the body-weight increment data by a predetermined rate, as the body-fat increment data.

Preferably, the body-weight-increment data acquisition means includes body-weight data acquisition means for acquiring data about current body weight of the subject, pre-pregnancy body-weight data acquisition means for acquiring data about body weight of the subject in the pre-pregnancy state, and body-weight-increment data calculation means for calculating the body-weight increment data based on the current body weight data and the pre-pregnancy body weight data.

Preferably, the basal-metabolism-increment determination means includes basal-metabolism data acquisition means for acquiring data about current basal metabolism of the subject, pre-pregnancy basal-metabolism data acquisition means for acquiring data about basal metabolism of the subject in the pre-pregnancy state, and basal-metabolism-increment calculation means for calculating the increment of basal metabolism based on the current basal metabolism data and the pre-pregnancy basal metabolism data.

Preferably, the basal-metabolism data acquisition means includes age data acquisition means for acquiring data about age of the subject, fetal-region-weight data acquisition means for acquiring data about fetal-region weight in the subject, maternal fat-free-mass data acquisition means for acquiring data about maternal fat-free mass of the subject, and basal-metabolism calculation means for calculating the basal metabolism data based on the age data, the fetal-region weight data and the maternal fat-free mass data.

Preferably, the maternal fat-free-mass data acquisition means includes body-weight data acquisition means for acquiring data about current body weight of the subject, maternal-weight data calculation means for calculating data about maternal weight of the subject based on the current body weight data and the fetal-region weight data acquired by the fetal-region-weight data acquisition means, body-height data acquisition means for acquiring data about body height of the subject, impedance data acquisition means for acquiring data about body impedance of the subject, and maternal fat-free-mass data calculation means for calculating the maternal fat-free mass data based on the maternal weight data, the body height data and the impedance data.

Preferably, the fetal-region-weight data acquisition means includes fetal-region-weight data determination means for determining the fetal-region weight data based on the elapsed pregnancy-period data acquired by the elapsed-pregnancy-period data acquisition means.

Preferably, the pre-pregnancy basal-metabolism data acquisition means includes pre-pregnancy age data acquisition means for acquiring data about age of the subject in the pre-pregnancy state, pre-pregnancy fat-free-mass data acquisition means for acquiring data about fat-free mass of the subject in the pre-pregnancy state, and pre-pregnancy basal-metabolism data calculation means for calculating the pre-pregnancy basal metabolism data based on the pre-pregnancy age data and the pre-pregnancy fat-free mass data.

Preferably, the pre-pregnancy fat-free-mass data acquisition means includes pre-pregnancy body-weight data acquisition means for acquiring data about body weight of the subject in the pre-pregnancy state, pre-pregnancy fat-mass data acquisition means for acquiring data about fat mass of the subject in the pre-pregnancy state, and pre-pregnancy fat-fee-mass calculation means for calculating the pre-pregnancy fat-free mass data based on the pre-pregnancy body weight data and the pre-pregnancy fat mass data.

Preferably, the pre-pregnancy fat-mass data acquisition means includes maternal fat-mass data acquisition means for acquiring data about maternal fat mass of the subject, body-fat-increment data acquisition means for acquiring data about body-fat increment of the subject in the pregnancy period, and pre-pregnancy fat-mass data calculation means for calculating the pre-pregnancy fat mass data based on the maternal fat mass data and the body-fat increment data.

Preferably, the maternal fat-mass data acquisition means includes body-weight data acquisition means for acquiring data about current body weight of the subject, fetal-region-weight data acquisition means for acquiring data about fetal-region weight in the subject, maternal-weight data calculation means for calculating data about maternal weight of the subject based on the current body weight data and the fetal-region weight data, body-height data acquisition means for acquiring data about body height of the subject, impedance data acquisition means for acquiring data about body impedance of the subject, and maternal fat-mass data calculation means for calculating the maternal fat mass data based on the maternal weight data, the body height data and the impedance data.

Preferably, the fetal-region-weight data acquisition means includes fetal-region-weight data determination means for determining the fetal-region weight data based on the elapsed pregnancy-period data acquired by the elapsed-pregnancy-period data acquisition means.

Preferably, the body-fat-increment data acquisition means includes body-weight-increment data acquisition means for acquiring data about body-weight increment of the subject in the pregnancy period, and body-fat-increment data determination means for determining a value obtained by multiplying the body-weight increment data by a predetermined rate, as the body-fat increment data.

Preferably, the body-weight-increment data acquisition means includes body-weight data acquisition means for acquiring data about current body weight of the subject, and body-weight-increment data calculation means for calculating the body-weight increment data based on the current body weight data and the pre-pregnancy body weight data acquired by the pre-pregnancy body-weight data acquisition means.

Preferably, the pre-pregnancy energy-expenditure determination means includes pre-pregnancy basal-metabolism data acquisition means for acquiring data about basal metabolism of the subject in the pre-pregnancy state, daily-activity-intensity data acquisition means for acquiring data about daily activity intensity of the subject, and pre-pregnancy energy-expenditure estimation means for estimating the pre-pregnancy energy expenditure based on the pre-pregnancy basal metabolism data and the daily activity intensity data.

Preferably, the pre-pregnancy basal-metabolism data acquisition means includes pre-pregnancy age data acquisition means for acquiring data about age of the subject in the pre-pregnancy state, pre-pregnancy fat-free-mass data acquisition means for acquiring data about fat-free mass of the subject in the pre-pregnancy state, and pre-pregnancy basal-metabolism data calculation means for calculating the pre-pregnancy basal metabolism data based on the pre-pregnancy age data and the pre-pregnancy fat-free mass data.

Preferably, the pre-pregnancy fat-free-mass data acquisition means includes pre-pregnancy body-weight data acquisition means for acquiring data about body weight of the subject in the pre-pregnancy state, pre-pregnancy fat-mass data acquisition means for acquiring data about fat mass of the subject in the pre-pregnancy state, and pre-pregnancy fat-fee-mass calculation means for calculating the pre-pregnancy fat-free mass data based on the pre-pregnancy body weight data and the pre-pregnancy fat mass data.

Preferably, the pre-pregnancy fat-mass data acquisition means includes maternal fat-mass data acquisition means for acquiring data about maternal fat mass of the subject, body-fat-increment data acquisition means for acquiring data about body-fat increment of the subject in the pregnancy period, and pre-pregnancy fat-mass data calculation means for calculating the pre-pregnancy fat mass data based on the maternal fat mass data and the body-fat increment data.

Preferably, the maternal fat-mass data acquisition means includes body-weight data acquisition means for acquiring data about current body weight of the subject, fetal-region-weight data acquisition means for acquiring data about fetal-region weight in the subject, maternal-weight data calculation means for calculating data about maternal weight of the subject based on the current body weight data and the fetal-region weight data, body-height data acquisition means for acquiring data about body height of the subject, impedance data acquisition means for acquiring data about body impedance of the subject, and maternal fat-mass data calculation means for calculating the maternal fat mass data based on the maternal weight data, the body height data and the impedance data.

Preferably, the fetal-region-weight data acquisition means includes fetal-region-weight data determination means for determining the fetal-region weight data based on the elapsed pregnancy-period data acquired by the elapsed-pregnancy-period data acquisition means.

Preferably, the body-fat-increment data acquisition means includes body-weight-increment data acquisition means for acquiring data about body-weight increment of the subject in the pregnancy period, and body-fat-increment data determination means for determining a value obtained by multiplying the body-weight increment data by a predetermined rate, as the body-fat increment data.

Preferably, the body-weight-increment data acquisition means includes body-weight data acquisition means for acquiring data about current body weight of the subject, and body-weight-increment data calculation means for calculating the body-weight increment data based on the current body weight data and the pre-pregnancy body weight data acquired by the pre-pregnancy body-weight data acquisition means.

According to a third aspect of the present invention, there is provided a maternity biodata measurement system for measuring biodata of a pregnant woman who is a subject, which comprises basal-metabolism data acquisition means for acquiring data about current basal metabolism of the subject, daily-activity-intensity data acquisition means for acquiring data about daily activity intensity of the subject, increased-fat-tissue-required energy-amount determination means for determining an energy amount required for increased maternal fat-tissue of the subject due to the pregnancy, and pregnancy intake-energy-amount determination means for determining an energy amount which is actually taken by the subject in the pregnancy period, based on the basal metabolism data, the daily activity intensity data, and the increased-fat-tissue-required energy amount. The increased-fat-tissue-required energy-amount determination means includes elapsed-pregnancy-period data acquisition means for acquiring data about elapsed period from the pregnancy of the subject, body-fat-increment data acquisition means for acquiring data about body-fat increment of the subject in the pregnancy period, and increased-tissue-required energy-amount estimation means for estimating the increased-tissue-required energy amount based on the elapsed pregnancy-period data and the body-fat increment data.

In the maternity biodata measurement system set forth in the third aspect of the present invention, it is preferable that the increased-fat-tissue-required energy-amount estimation means includes estimation-equation storage means for storing an estimation equation for calculating data about energy amount required for an increased fat tissue due to the pregnancy, using body-fat increment data as a parameter, estimation-equation execution means for assigning the acquired body-fat increment data to the estimation equation to calculate the energy amount data required for the increased fat tissue due to the pregnancy, and increased-fat-tissue-required energy-amount calculation means for calculating the increased-fat-tissue-required energy amount based on the calculated energy amount data and the acquired elapsed pregnancy-period data.

In the maternity biodata measurement system set forth in the third aspect of the present invention, it is preferable that the body-fat-increment data acquisition means includes body-weight-increment data acquisition means for acquiring data about body-weight increment of the subject in the pregnancy period, and body-fat-increment data determination means for determining a value obtained by multiplying the body-weight increment data by a predetermined rate, as the body-fat increment data.

Preferably, the body-weight-increment data acquisition means includes body-weight data acquisition means for acquiring data about current body weight of the subject, and body-weight-increment data calculation means for calculating the body-weight increment data based on the current body weight data and pre-pregnancy body weight data.

Preferably, the basal-metabolism data acquisition means includes age data acquisition means for acquiring data about age of the subject, fetal-region-weight data acquisition means for acquiring data about fetal-region weight in the subject, maternal fat-free-mass data acquisition means for acquiring data about maternal fat-free mass of the subject, and basal-metabolism calculation means for calculating the basal metabolism data based on the age data, the fetal-region weight data and the maternal fat-free mass data.

Preferably, the maternal fat-free-mass data acquisition means includes body-weight data acquisition means for acquiring data about current body weight of the subject, maternal-weight data calculation means for calculating data about maternal weight of the subject based on the current body weight data and the fetal-region weight data acquired by the fetal-region-weight data acquisition means, body-height data acquisition means for acquiring data about body height of the subject, impedance data acquisition means for acquiring data about body impedance of the subject, and maternal fat-free-mass data calculation means for calculating the maternal fat-free mass data based on the maternal weight data, the body height data and the impedance data.

Preferably, the fetal-region-weight data acquisition means includes fetal-region-weight data determination means for determining the fetal-region weight data based on the elapsed pregnancy-period data acquired by the elapsed-pregnancy-period data acquisition means.

In the maternity biodata measurement system set forth in the first aspect of the present invention, a sum of a pre-pregnancy energy expenditure and a pregnancy extra energy amount of a subject, is determined as an energy amount necessary for the subject in a pregnancy period. In particular, the pregnancy extra energy amount is determined based on pre-pregnancy body-mass index data and elapsed pregnancy-period data about the subject. This makes it possible to determine the necessary energy amount as a value appropriate for the subject. Thus, this maternity biodata measurement system allows a necessary energy amount for a pregnant woman to be measured on an individual basis so as to achieve the first object of the present invention.

In the maternity biodata measurement system set forth in the second aspect of the present invention, a sum of a pre-pregnancy energy expenditure of a subject, an increment of basal metabolism of the subject in a pregnancy period and an energy amount required for increased tissue of the subject due to pregnancy is determined as an intake energy amount of the subject in the pregnancy period. In particular, the increased-tissue-required energy amount is estimated based on subject's data about elapsed pregnancy-period and body-fat increment in the pregnancy period. This makes it possible to determine the intake energy amount as a value appropriate for the subject. Thus, this maternity biodata measurement system allows an intake energy amount for a pregnant woman to be measured on an individual basis so as to achieve the second object of the present invention.

In the maternity biodata measurement system set forth in the third aspect of the present invention, an intake energy amount of a subject in a pregnancy period is determined based on subject's data about current basal metabolism, a daily activity intensity, and an energy expenditure in increased fat-tissue due to pregnancy. In particular, the energy expenditure in the increased fat-tissue is estimated based on subject's data about elapsed pregnancy-period and body-fat increment in the pregnancy period. This makes it possible to determine the intake energy amount as a value appropriate for the subject. Thus, this maternity biodata measurement system also allows an intake energy amount for a pregnant woman to be measured on an individual basis so as to achieve the second object of the present invention.

Further, the maternity biodata measurement system having all features of the specific preferred embodiments in the first to third aspects of the present invention makes it possible to measure a necessary energy amount for a pregnant woman and/or an intake energy amount of the pregnant woman in a simple and easy manner, using only relatively easily acquirable data about the subject.

Further, the maternity biodata measurement system having both features of the first aspect of the present invention and the second or third aspect of the present invention makes it possible to measure excess and deficiency in intake energy amount based on a necessary energy amount for a pregnant woman and/or an intake energy amount of the pregnant woman on an individual basis and in a simple and easy manner.

BRIEF DESCRIPTION OF DRAWINGS

FIG. 9 is a chart showing one example of a print output in the biodata measurement apparatus 1.

FIG. 14 is a graph showing a relationship between a fetal-region weight and an elapsed number of pregnancy weeks.

BEST MODE FOR CARRYING OUT THE INVENTION

A maternity biodata measurement system according to a first aspect of the present invention is designed to determine a sum of a pre-pregnancy energy expenditure of a subject and a suitable extra energy expenditure to be added to the pre-pregnancy energy expenditure in a pregnancy period, as an energy amount necessary for the subject in the pregnancy period and particularly to estimate the pregnancy extra energy amount based on pre-pregnancy body-mass index data and elapsed pregnancy-period data about the subject. A relationship of the pregnancy extra energy amount, the pre-pregnancy body-mass index data and the elapsed pregnancy-period data is based on the following knowledge.

With the cooperation of a large number, specifically about 500, of healthy pregnant women, the inventors measured various body composition data, such as a body weight and a fat mass of each pregnant woman. Then, the measured body composition data were divided into five groups depending on whether each pregnant woman has a body-mass index in a pre-pregnancy state (pre-pregnancy body-mass index: a value obtained by dividing a body weight in the pre-pregnant state by a square value of a body height) of less than 18; 18 to less than 21; 21 to less than 24; 24 to less than 26; or 26 or more, and averaged in each of the groups.

Then, an energy expenditure per day increased in a period from the pre-pregnant state up to the point of each measurement was calculated using the averaged body composition data as basic data. The energy expenditure calculated based on the body composition data of the many healthy pregnant women can be regarded as a suitable energy amount to be added in a pregnancy period which is applicable to any other pregnant women belonging to the same body-mass index group.

Figure 12:
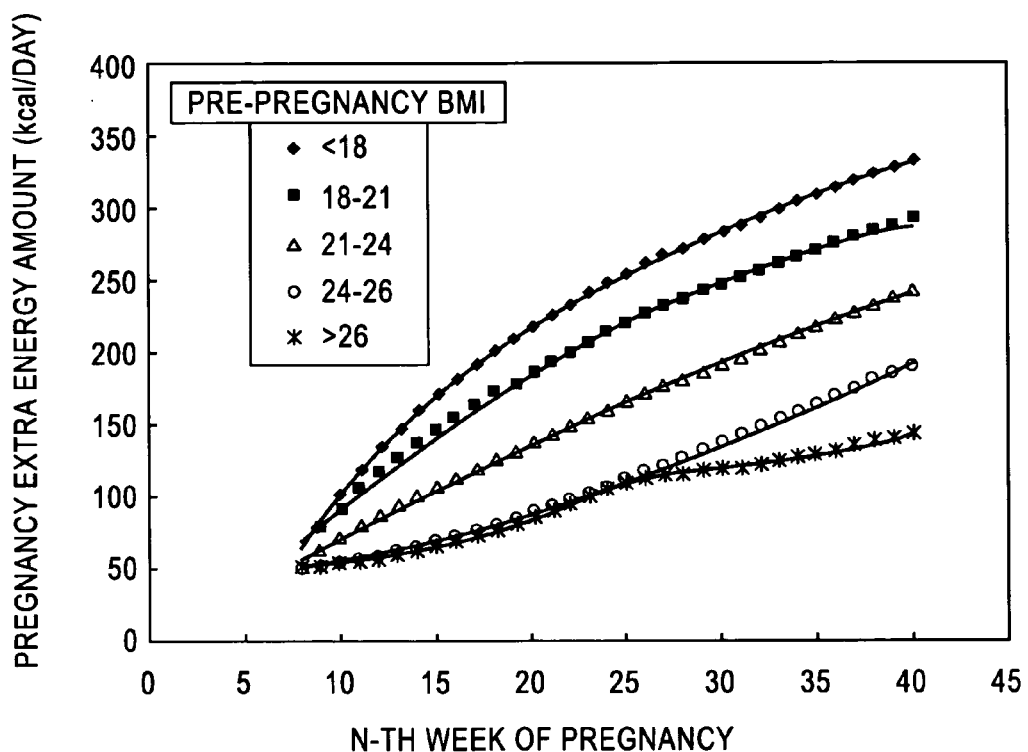
FIG. 12 is a graph showing a relationship between a pregnancy extra energy amount and an elapsed number of pregnancy weeks.

This energy amount to be added in a pregnancy period (pregnancy extra energy amount) was plotted on a graph which has a vertical axis representing an energy amount (Kcal/day) and a horizontal axis representing an elapsed number of pregnancy weeks (n-th week of pregnancy), to obtain the result as shown in FIG. 12. In FIG. 12, an energy amount in a pregnancy week insufficient in basic data was obtained using an interpolation technique. Further, a pregnancy extra energy amount in the 2nd week of pregnancy is set at zero kcal/day in consideration of a relationship between a typical woman's menstrual cycle and a conception day.

As seen in FIG. 12, the pregnancy extra energy amount can be expressed by the following polynomial estimation equation Gn using an elapsed number of pregnancy weeks as a parameter: pregnancy extra energy amount=an×(elapsed number of pregnancy weeks)$^2$+bn×elapsed number of pregnancy weeks+cn, wherein each of an, bn and cn is a constant deferent in each of the body-mass index groups.

Thus, in the maternity biodata measurement system according to the first aspect of the present invention, preferably, the pregnancy extra-energy-amount determination means includes estimation-equation storage means for storing a plurality of estimation equations Gn for calculating the pregnancy extra energy amount using elapsed pregnancy-period data as a parameter, in association with pre-pregnancy body-mass index data, estimation-equation selection means for selecting one of the estimation equations corresponding to the acquired pre-pregnancy body-mass index data, and estimation-equation execution means for assigning the acquired elapsed pregnancy-period data to the selected estimation equation to calculate the pregnancy extra energy amount.

A maternity biodata measurement system according to a second aspect of the present invention is designed to determine a sum of a pre-pregnancy energy expenditure of a subject, an increment of basal metabolism of the subject in a pregnancy period and an energy amount required for increased tissue of the subject due to pregnancy, as an intake energy amount of the subject in the pregnancy period. In particular, this maternity biodata measurement system is designed to estimate the increased-tissue-required energy amount based on subject's data about elapsed pregnancy-period and body-fat increment in the pregnancy period. A relationship of the increased-tissue-required energy amount, the elapsed pregnancy-period data and the body-fat increment data is based on the following knowledge.

Firstly, an energy amount actually taken by a pregnant woman can be paraphrased as an energy amount necessary for the pregnant woman. As disclosed in the Non-Patent Publications 2 and 3, an energy amount necessary for a pregnant woman is a value obtained by adding an increment in basal metabolism associated with hypermetabolism and an energy amount requited for increased tissue due to pregnancy to an energy amount expended by the pregnant woman in a pre-pregnant state. The increased tissue due to pregnancy includes protein increased in fetus, placenta and maternal body and fat tissue increased in the maternal body.

Figure 5:
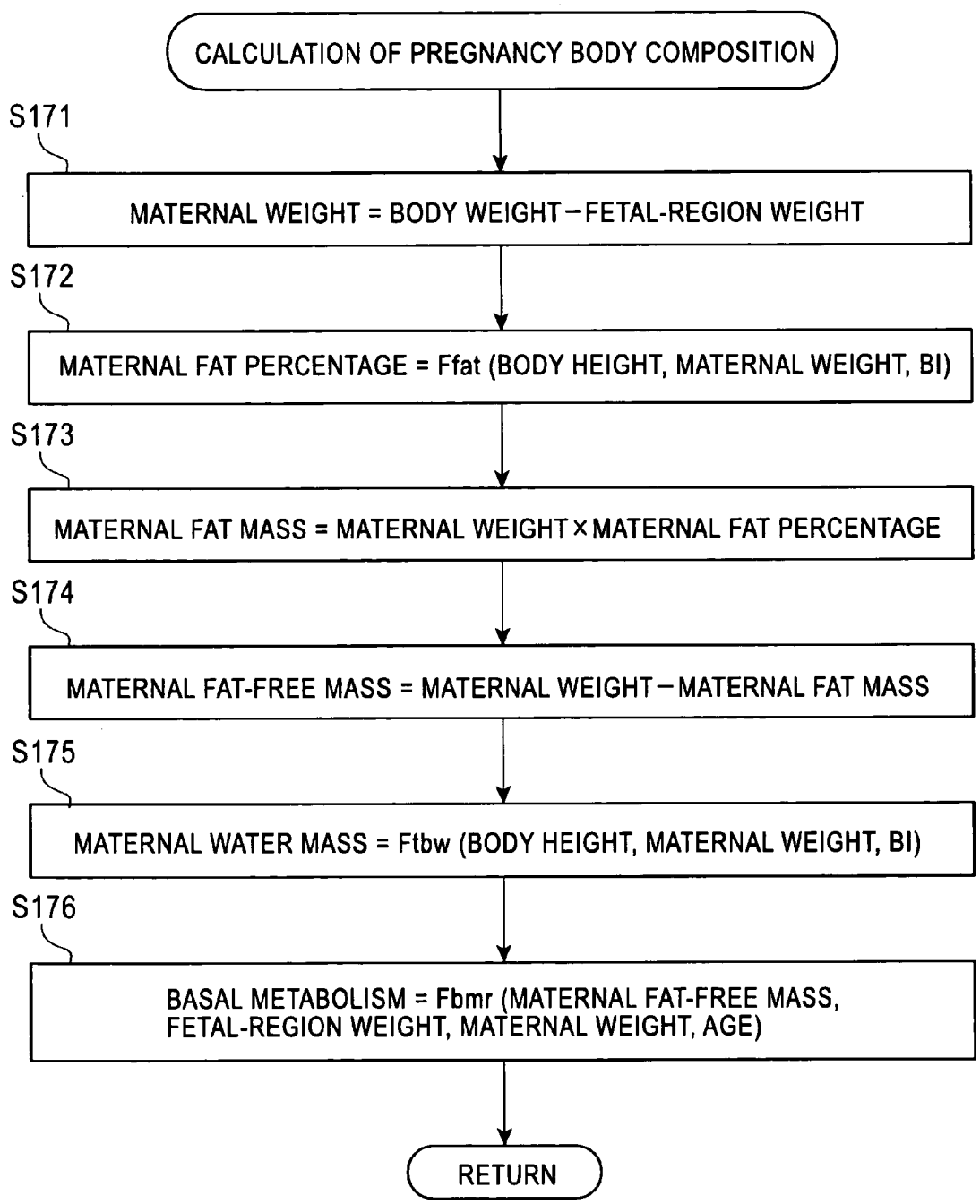
FIG. 5 is a flowchart showing a subroutine of the operation/calculation program to be executed in the biodata measurement apparatus 1.
Figure 6:
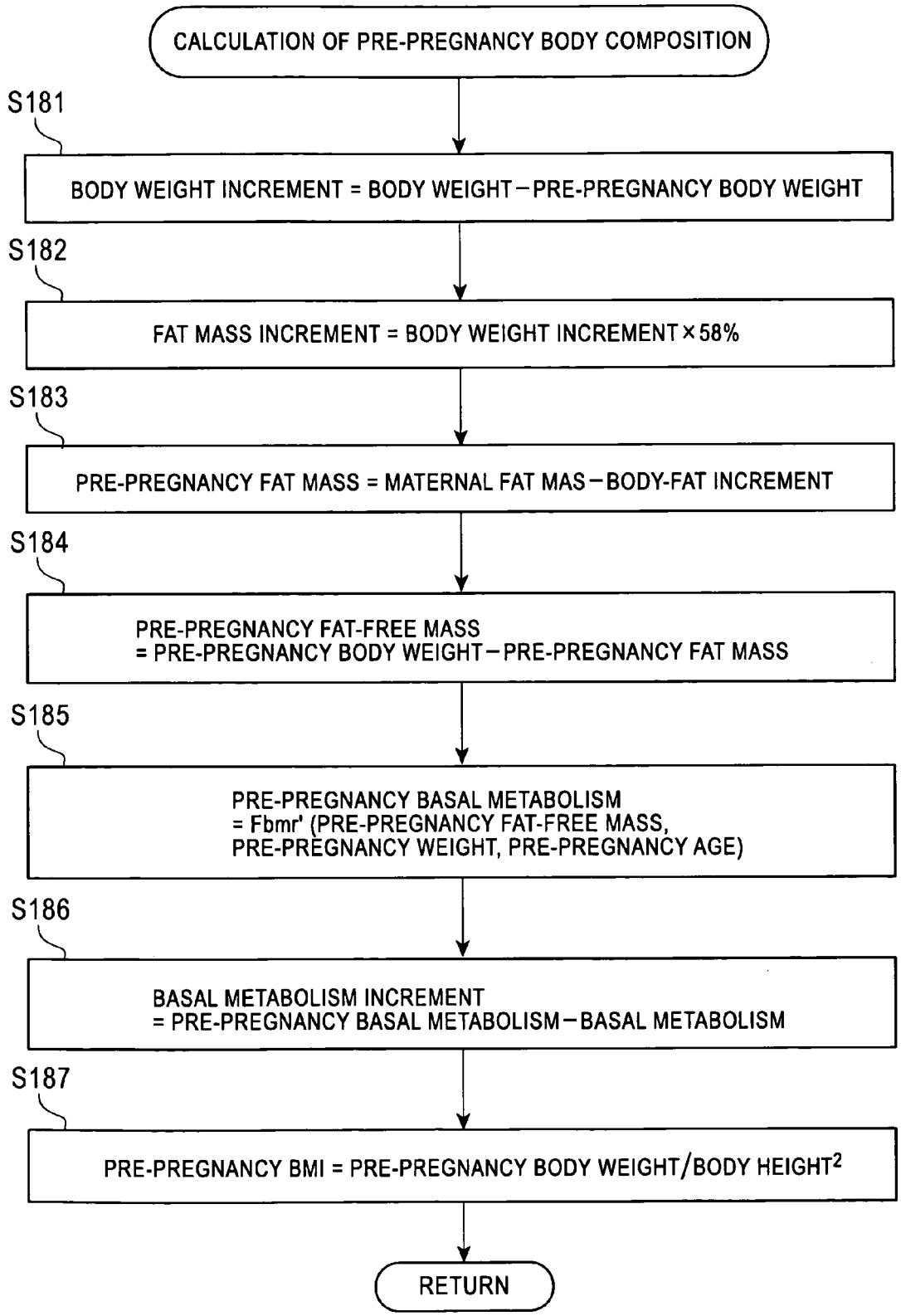
FIG. 6 is a flowchart showing a subroutine of the operation/calculation program to be executed in the biodata measurement apparatus 1.
Figure 7:
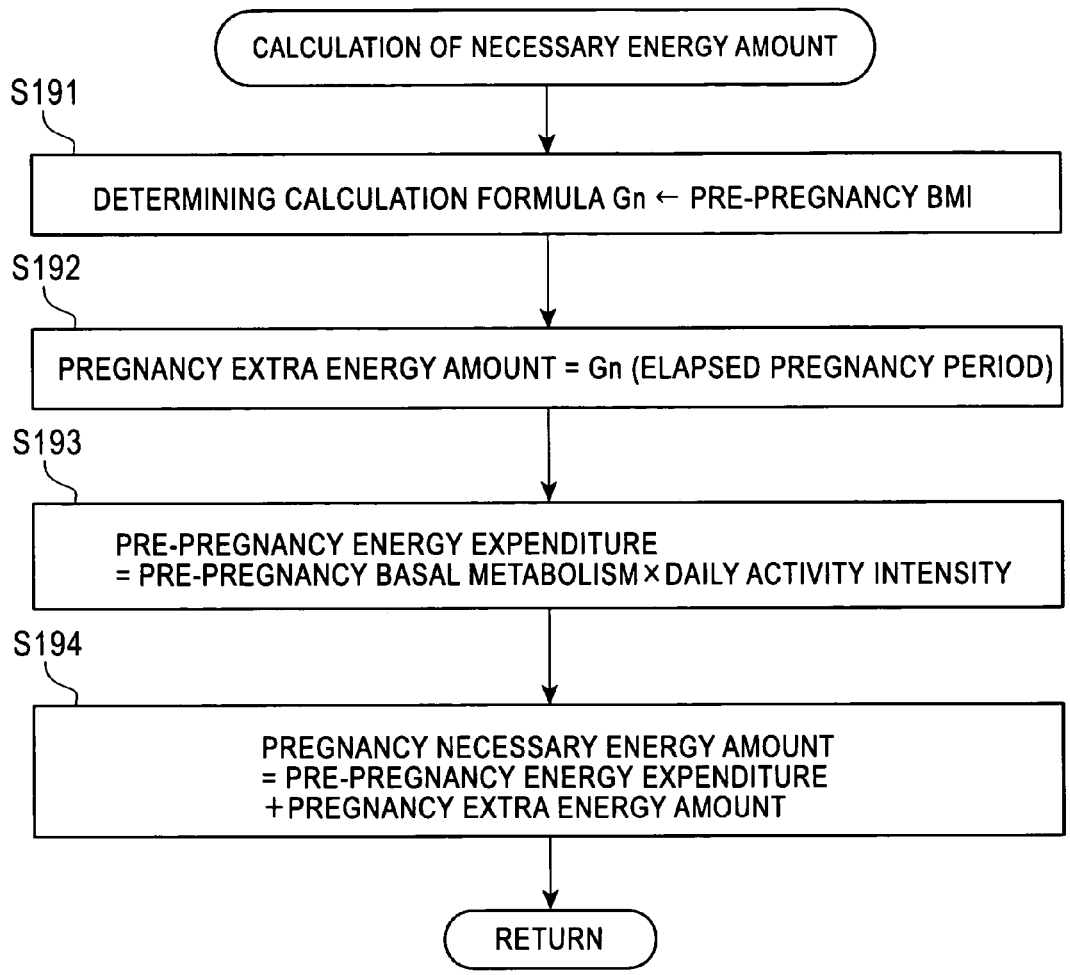
FIG. 7 is a flowchart showing a subroutine of the operation/calculation program to be executed in the biodata measurement apparatus 1.
Figure 8:
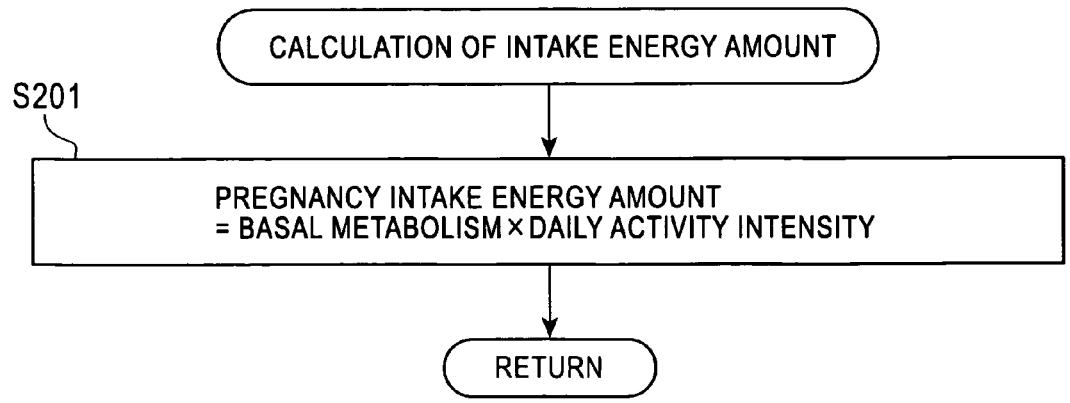
FIG. 8 is a flowchart showing a subroutine of the operation/calculation program to be executed in the biodata measurement apparatus 1.
Figure 13:
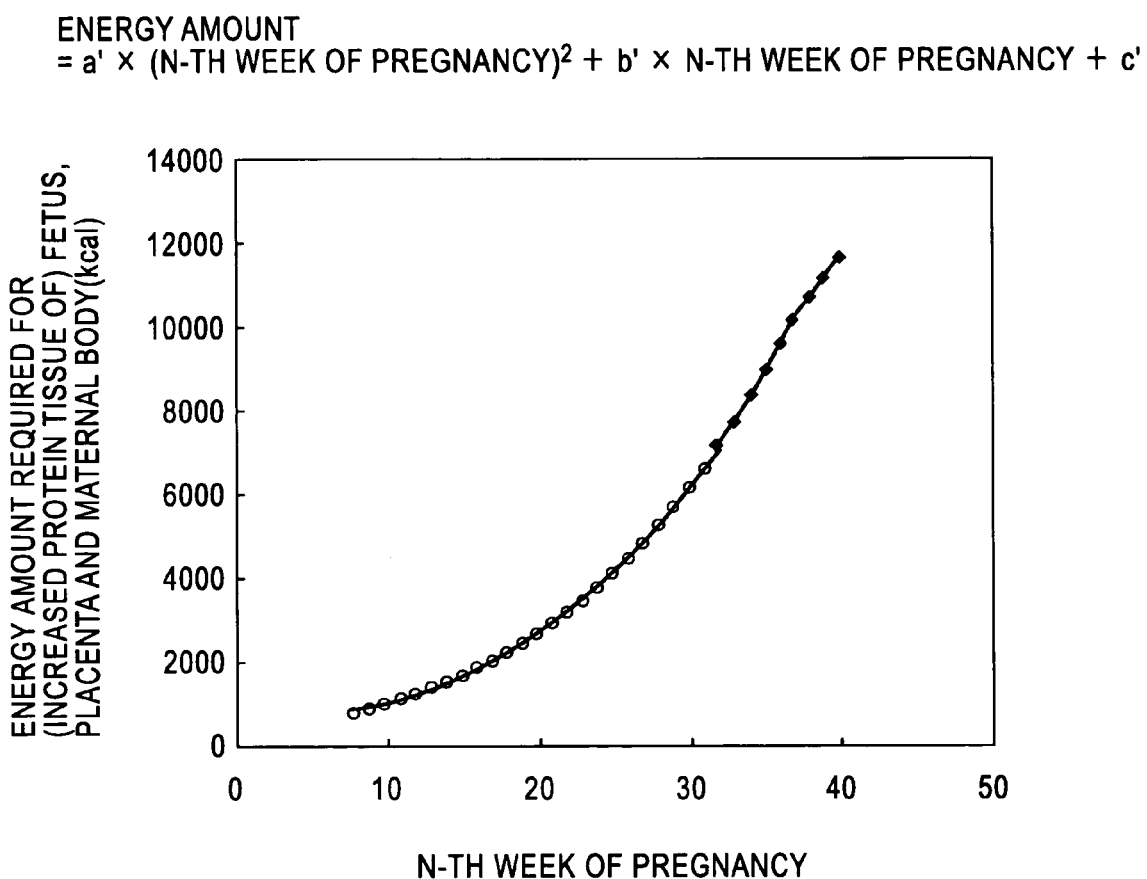
FIG. 13 is a graph showing a relationship between an elapsed number of pregnancy weeks and an energy amount required for increments of protein in fetus, placenta and maternal body due to pregnancy.

Among them, the protein in fetus, placenta, and maternal body tends to increase approximately in proportion to an elapsed number of pregnancy weeks. However, as disclosed, for example, in FIG. 5 of the Patent Publication 1, the protein about fetus will increase as a quadratic function in response to an elapsed number of pregnancy weeks. As the result of inventers' researches in view of these facts, it has been found that an energy amount required for an increment in the protein of fetus, placenta and maternal body (vertical axis: kcal) can be expressed by the following quadratic polynomial estimation equation G using an elapsed number of pregnancy weeks (horizontal axis) as a parameter: energy amount=a'×(elapsed number of pregnancy weeks)$^2$+b'× elapsed number of pregnancy weeks+c', as shown in FIG. 13. In the estimation equation G each of an, bn and cn is a constant.

Further, considering that an energy amount necessary for burning 1 kg of fat is about 7200 kcal (as is well known), an energy amount required for the fat tissue increased in maternal body can be calculated by multiplying a body-fat increment of the pregnant woman in a pregnancy period by the 7200 kcal. An body-fat increment is obviously varied depending on pregnant women. Thus, an energy required for fat tissue increased in maternal body will be calculated based on an estimation equation using a body-fat increment as a parameter.

Each of an energy amount required for an increment in the protein of fetus, placenta and maternal body and an energy amount required for the fat tissue increased in maternal body to be calculated using the above estimation equations is a cumulative energy amount in a pregnancy period. Therefore, in an operation for calculating an increased-tissue-required energy amount per day based on these energy amounts, it is required to perform a calculation based on an elapsed pregnancy-period, for example, an operation of dividing each of the energy amounts by an elapsed number of days of pregnancy.

Thus, in the maternity biodata measurement system according to the second aspect of the present invention, preferably, the increased-tissue-required energy-amount estimation means includes first estimation-equation storage means for storing an estimation equations for calculating first energy amount data (i.e., an energy amount required for an increment in the protein of fetus, placenta and maternal body) using elapsed pregnancy-period data as a parameter, first estimation-equation execution means for assigning the acquired elapsed pregnancy-period data to the first estimation equation to calculate the first energy amount data, second estimation-equation storage means for storing an estimation equations for calculating second energy amount data (i.e., an energy amount required for the fat tissue increased in maternal body) using body-fat increment data as a parameter, second estimation-equation execution means for assigning the acquired body-fat increment data to the second estimation equation to calculate the second energy amount data, and increased-tissue-required energy-amount calculation means for calculating the increased-tissue-required energy amount based on the acquired elapsed pregnancy-period data and a sum of the first energy amount data and the second energy amount data.

A maternity biodata measurement system according to a third aspect of the present invention is designed to determine an intake energy amount of a subject in a pregnancy period based on subject's data about current basal metabolism, a daily activity intensity, and an energy amount required for increased fat-tissue due to pregnancy and particularly to estimate the increased-fat-tissue-required energy amount based on subject's data about elapsed pregnancy-period and body-fat increment in the pregnancy period. A relationship of the increased-tissue-required energy amount, the elapsed pregnancy-period data and the body-fat increment data is based on the following knowledge.

As is well known, for example, as disclosed in the Non-Patent Publication 1, an energy expenditure of a subject other than a pregnant woman is typically calculated by multiplying a basal metabolism of the subject by a daily activity intensity of the subject. In view of this fact, an energy amount obtained by multiplying a current basal metabolism of a pregnant woman by a daily activity intensity of the pregnant woman can be regarded as an energy amount actually expended (i.e., actually taken) by the pregnant woman.

However, if a current basal metabolism of a pregnant woman is measured, for example, by the technique disclosed in the Patent Publication 4, or a current basal metabolism of a pregnant woman is estimated primarily based on a maternal fat-free mass, a fetal-region weight and an age of the pregnant woman, it is likely to cause a problem about lack of an energy amount required for increased fat tissue due to pregnancy.

In view of solving this problem, it is desirable to conduct a calculation based on an elapsed pregnancy-period, specifically, a calculation of a necessary energy amount, particularly, for the fat tissue among the increased tissue due to pregnancy, based on the estimation equation using an increment of fat mass, and dividing the calculated energy amount by an elapsed number of days of pregnancy, to obtain an increased-fat-tissue-required energy amount per day, and then add the calculated energy amount to the energy amount obtained by multiplying a current basal metabolism of the pregnant woman by a daily activity intensity of the pregnant woman.

Thus, in the maternity biodata measurement system according to the third aspect of the present invention, preferably, the increased-fat-tissue-required energy-amount estimation means includes estimation-equation storage means for storing an estimation equation G for calculating data about energy amount required for an increased fat tissue due to the pregnancy, using body-fat increment data as a parameter, estimation-equation execution means for assigning said acquired body-fat increment data to the estimation equation to calculate the energy amount data required for the increased fat tissue due to the pregnancy, and increased-fat-tissue-required energy-amount calculation means for calculating the increased-fat-tissue-required energy amount based on the calculated energy amount data and the acquired elapsed pregnancy-period data.

[First Embodiment]

With reference to FIGS. 1 to 9, a first embodiment of the present invention will now be described. The first embodiment is primarily based on the first aspect of the present invention.

Figure 1:
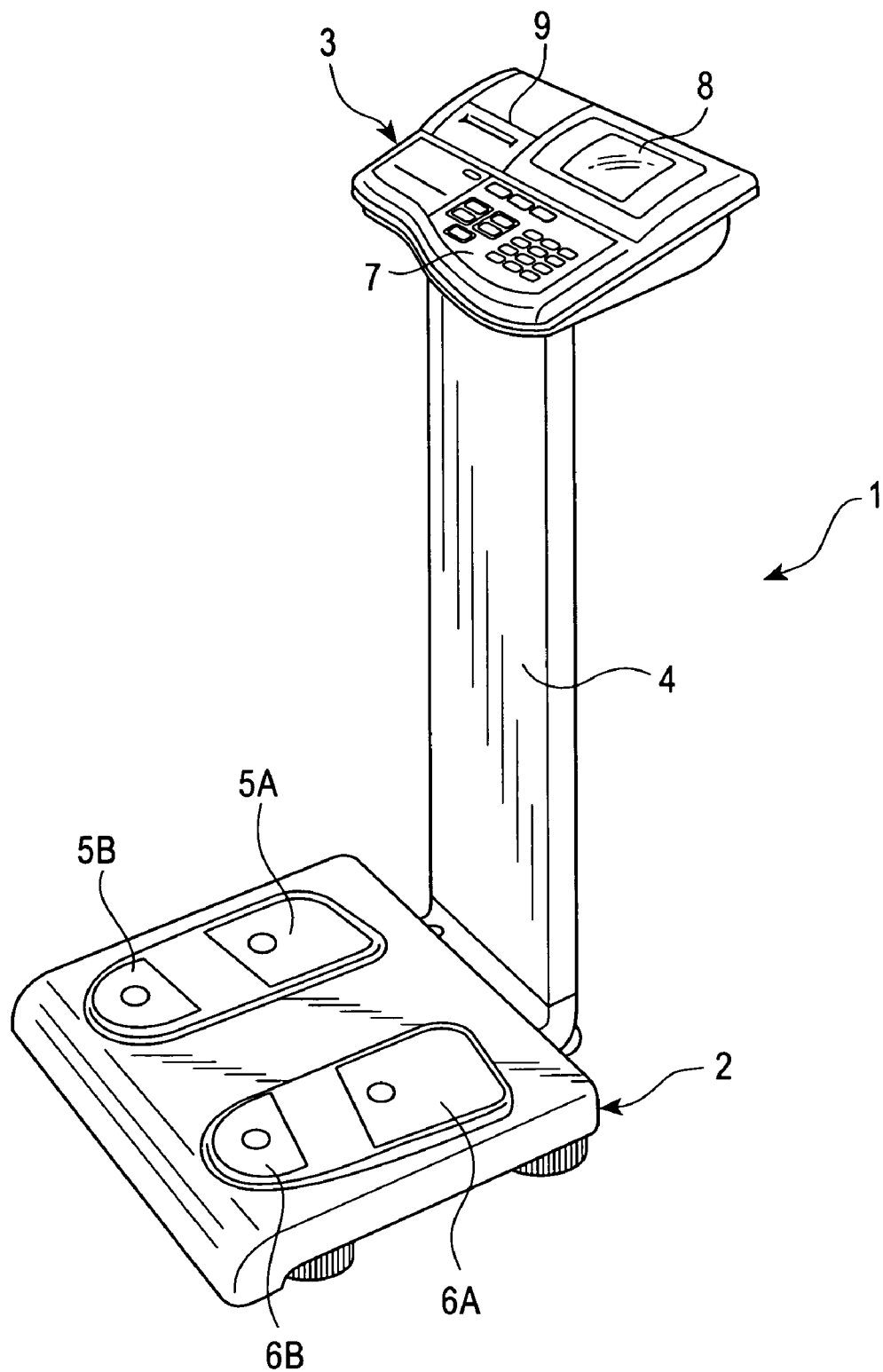
FIG. 1 is a perspective external view showing a biodata measurement apparatus 1 incorporating a maternity biodata measurement system according to a first embodiment of the present invention.
Figure 2:
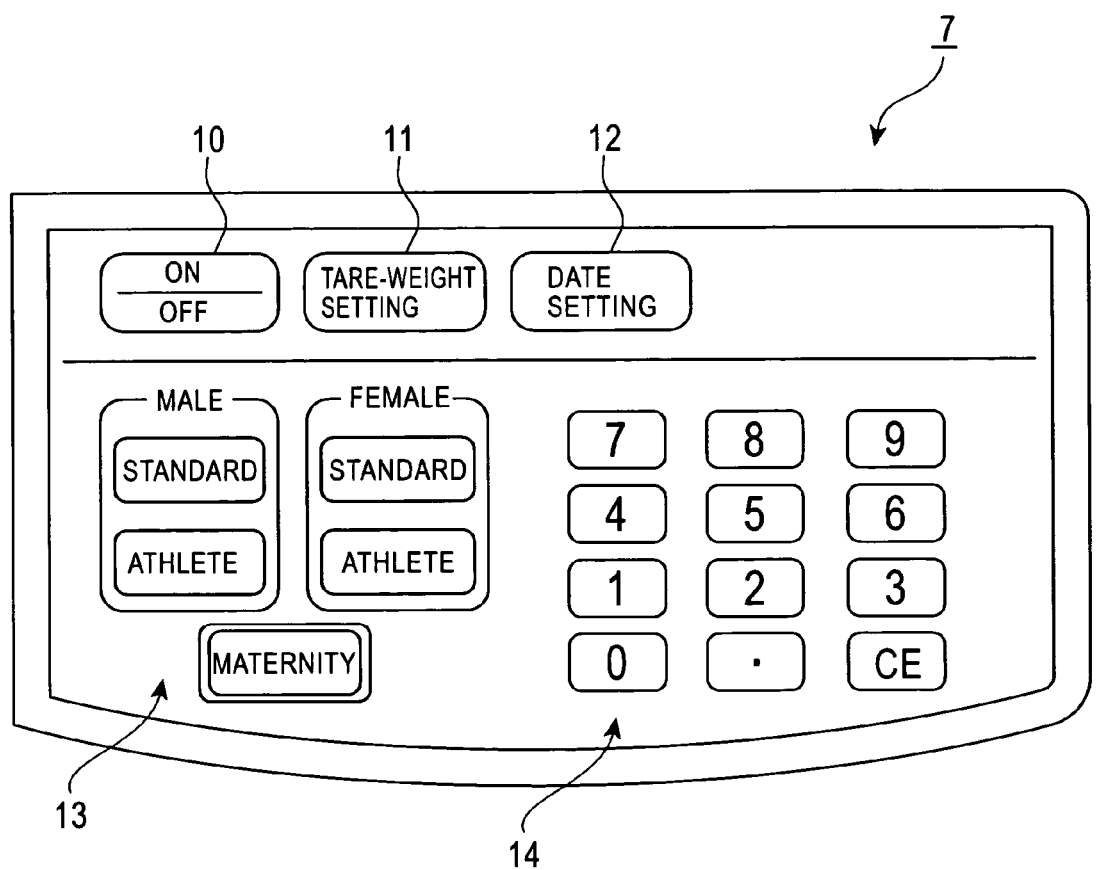
FIG. 2 is an enlarged view showing a manual operation section of the biodata measurement apparatus 1.
Figure 3:
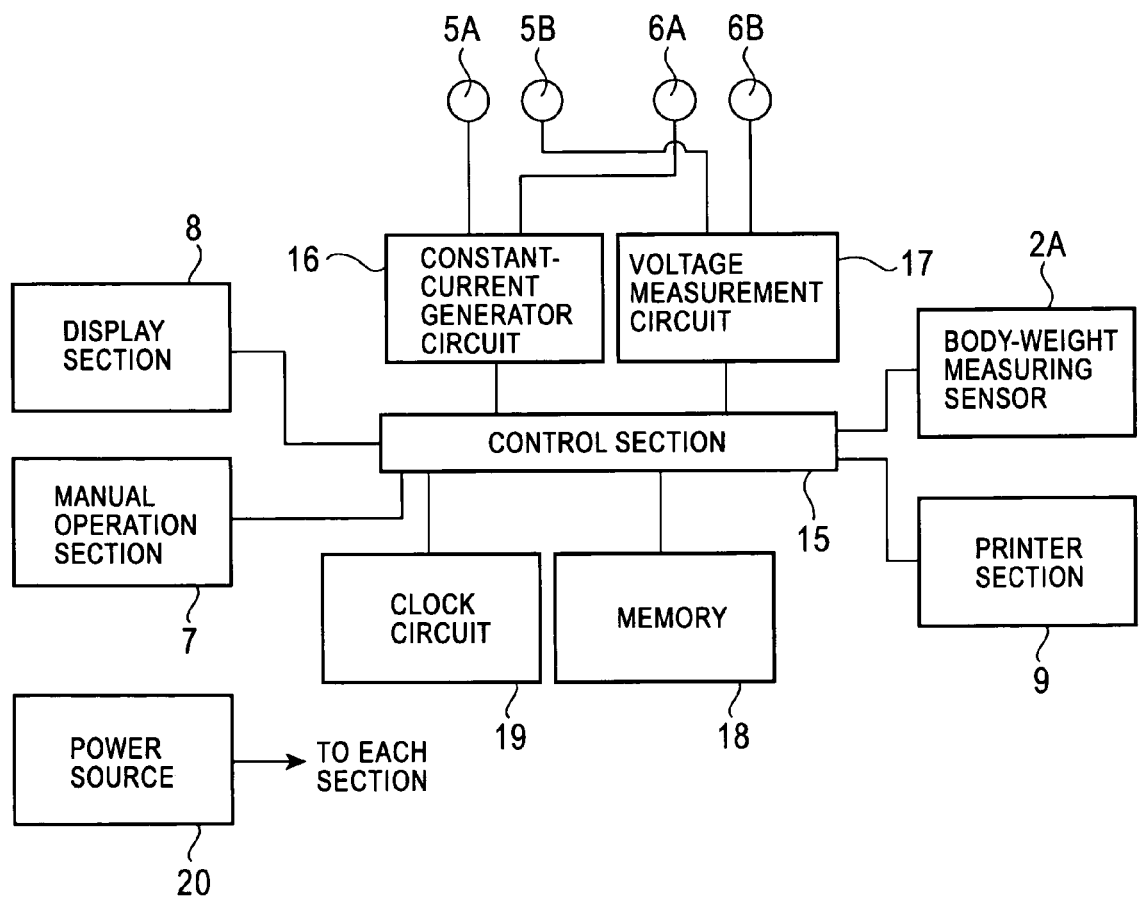
FIG. 3 is a schematic block diagram showing an electric circuit configuration of the biodata measurement apparatus 1.
Figure 4:
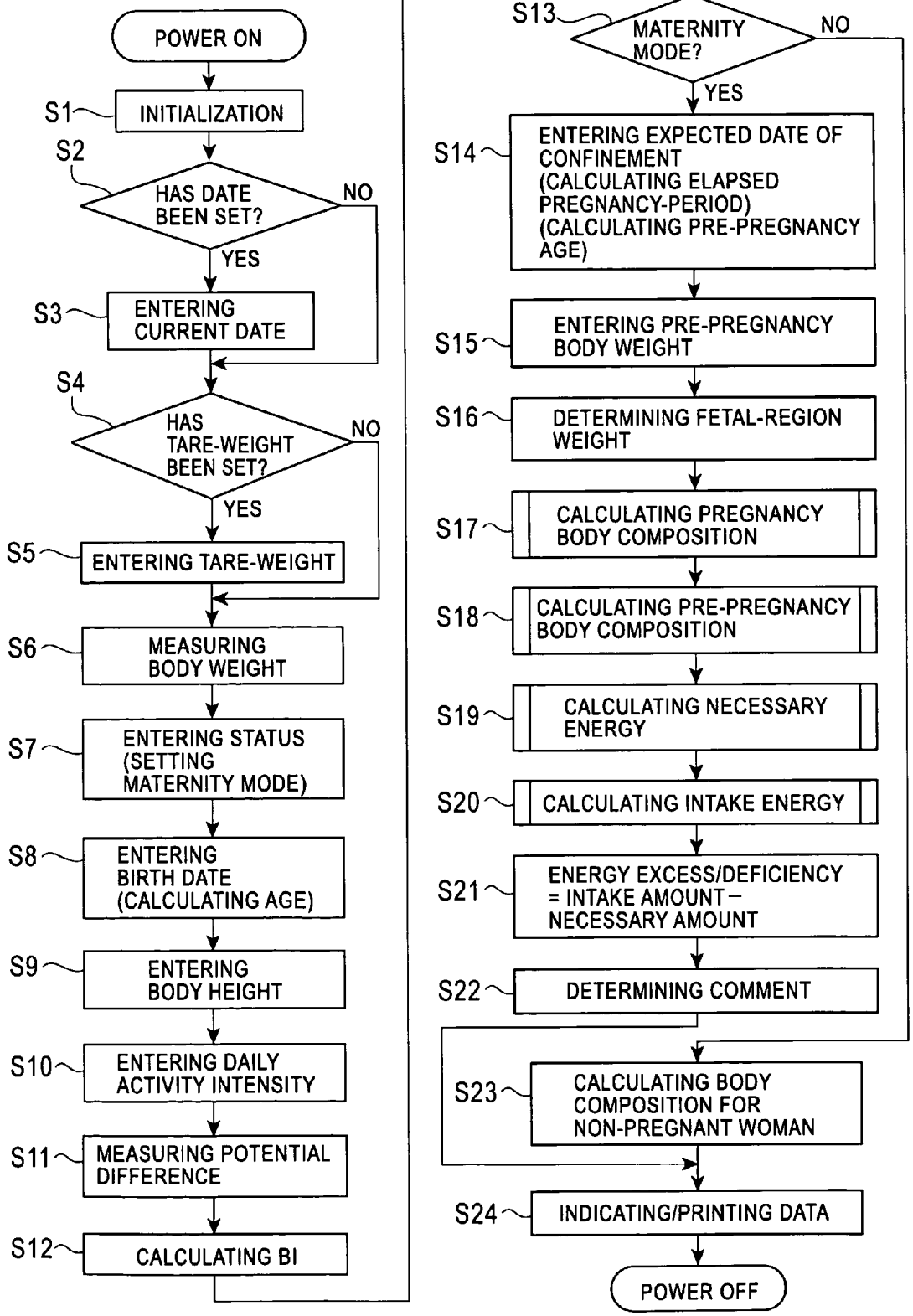
FIG. 4 is a flowchart showing a main routine of an operation/calculation program to be executed in the biodata measurement apparatus 1.

FIG. 1 is a perspective external view showing a biodata measurement apparatus 1 incorporating a maternity biodata measurement system according to the first embodiment. FIG. 2 is an enlarged view showing a manual operation section of the biodata measurement apparatus 1. FIG. 3 is a schematic block diagram showing an electric circuit configuration of the biodata measurement apparatus 1. FIG. 4 is a flowchart showing a main routine of an operation/calculation program to be executed in the biodata measurement apparatus 1. FIGS. 5 to 8 are flowcharts showing various subroutines of the operation/calculation program to be executed in the biodata measurement apparatus 1. FIG. 9 is a chart showing one example of a print output in the biodata measurement apparatus 1.

The biodata measurement apparatus 1 (hereinafter referred to simply as "apparatus 1") incorporating the maternity biodata measurement system according to the first embodiment is an improved type of a conventional body composition analyzer designed to calculate various body composition data of a subject, such as fat mass, fat-free mass, body water, muscle mass, bone mass and basal metabolism, based on a so-called bioelectric impedance method. The biodata measurement apparatus 1 comprises a mounting base 2 for allowing a subject to mount thereon in a standing posture, an input/output unit (I/O unit) 3 for allowing the subject himself/herself or an operator of this apparatus (hereinafter referred to collectively as "user") to input and output various data therethrough, and a column 4 fixing the I/O unit 3 to the mounting base 2 and housing wirings for electrically connecting therebetween.

The mounting base 2 houses a so-called "load cell" serving as a body-weight measuring sensor for detecting a load to be generated when the user mounts on the mounting base. The mounting base 2 has a top surface provided with a pair of electrodes 5A, 5B for bringing into contact with the bottom of the left foot of a subject and a pair of electrodes 6A, 6B for bringing into contact with the bottom of the right foot of the subject, in an electrically isolated state.

The I/O unit 3 comprises a manual operation section 7 including a switch panel to be manually operated by a user, a display section 8 including a liquid-crystal display screen for outputting images of various data acquired by the apparatus 1, and a printer section 9 including a thermal printer for outputting printed materials of the data. The switch panel of the manual operation section 7 includes a power key 10 for activating or deactivating the apparatus 1, a cloth-weight set key for setting a weight of clothes of a subject, a date set key 12 for setting a data, a status set key 13 for setting a sexuality and a physique type of a subject or whether a subject is a pregnant woman, and a numeric keypad 14 for setting a body height and birth date of a subject, an expected date of confinement of a subject, etc.

The I/O unit 3 internally has a control section 15 including a processor and a temporal memory for executing after-mentioned various operation/calculation programs and, a constant-current generator circuit 16 electrically connected to the electrodes 5A, 6A to supply a constant AC current to these electrodes, a voltage measurement circuit 17 electrically connected to the electrodes 5B, 6B to measure a potential difference between these electrodes, a memory 18 including a read-only masked memory storing the operation/calculation programs to be executed by the control section 15 and a rewritable flash memory for storing the result of the operation/calculation, etc., and a clock circuit 19 for controlling the timing of operations in the control section 15. Further, the I/O unit 3 houses a power source 20 for supplying power to be consumed by the control section 15 and other components of the apparatus 1.

The control section 15 is electrically connected to each of the body-weight measuring sensor 2A, the manual operation section 7, the display section 8, the printer section 9, the constant-current generator circuit 16, the voltage measurement circuit 17, the memory 18 and the clock circuit 19, so as to execute various operations/calculations, such as measurement of a body weight of a subject, receiving of manual inputs from a subject, current supply to the electrodes 5A, 6A, measurement of a potential difference between the electrodes 5B, 6B, measurement of a bioelectric impedance of a subject, calculation of a body composition based on the bioelectric impedance, and display and printing of the calculation result.

With reference to the flowcharts, an operation/calculation process to be executed in the apparatus 1 will be described below. When a user pushes down the power key 10 to activate the apparatus 1, the control section 15 executes an operation/calculation process illustrated in the flowchart in FIG. 4.

In Step S1, an initialization is performed. For example, previous measurement data temporarily stored on the temporal memory of the control section is deleted, and a flag of an after-mentioned maternity mode is reset. Simultaneously, the control section 15 acquires data about current date from the clock circuit 19 and reads initial cloth-weight data (e.g. 1.5 kg) from the memory 18 to indicate these data on the display section 8.

In Step S2, it is checked whether the date set key 13 has been pushed down. When the date set key 13 has been pushed down, the process advances to Step S4. If the date set key 13 has not been pushed down, the process skips Step S3 and advances to Step S4. In this process, if there is no need to change the current date data indicated on the display section 8, the user may omit the operation of pushing down the date set key 12.

In Step S3, data about current date is re-acquired. Specifically, if the user enters date data using the numeric keypad 14, the control section 15 receives the input from the numeric keypad 14, and replaces a current date in the clock circuit 19 with the entered date data. Subsequently, the clock circuit 19 will continue to time on the basis of the entered date data.

In Step S4, it is checked whether the cloth-weight set key 11 has been pushed down. When the cloth-weight set key 11 has been pushed down, the process advances to Step S5 and then to Step S6. If the cloth-weight set key 11 has not been pushed down, the process skips Step S5 and advances to Step S6. In this process, if there is no need to change the cloth weight data indicated on the display section 8, the user may omit the operation of pushing down the cloth-weight set key 11.

In Step S5, data about cloth weight of the subject is re-acquired. Specifically, if the user enters cloth weight data using the numeric keypad 14, the control section 15 receives the input from the numeric keypad 14, and replaces the initial cloth-weight data read from the memory 18 with the entered cloth weight data. The entered cloth weight data is stored on the temporal memory as an actual cloth weight of the subject, and will be used in an after-mentioned body-weight measurement operation.

In Step S6, data about body weight of the subject is acquired. Specifically, when the subject stands on the top surface of the mounting base 2, a load signal corresponding to a body weight of the subject is output from the body-weight measuring sensor 2A. Actually, this Step S6 is initiated in response to detecting the load signal by the control section 15. Then, data about current body weight of the subject is calculated by subtracting the cloth weight data from weight data corresponding to the detected load signal. In the following process, the subject will manually enter various date while standing on the top surface of the mounting base 2.

In Step S7, data about status of the subject is acquired. The control section 15 operates to indicate a sign or message for prompting to set sexuality and physique type of the subject, on the display section 8 together with the body weight data acquired in Step S6, and receives an input from the status set key 13. Specifically, when the user selects and pushes down one of five key switches consisting of "male standard", "male athlete", "female standard", "female athlete" and "maternity" which are included in the status set key, subject's status data is determined depending on the pushed key switch. In particular, if the key switch "maternity" is pushed down, a flag for executing a process for the after-mentioned maternity mode will be set. This flag has been reset in advance through the initialization in Step S1.

In Step S8, data about age of the subject is acquired. The control section 15 operates to indicate a sign or message for prompting to enter the birth date of the subject on the display section 8, and receives an input from the numeric keypad 14. Specifically, when the user enters data about birth date of the subject using the numeric keypad 14, data about age of the subject is calculated based on the entered birth date and the current date data. Instead of entry of the birth date data, the apparatus 1 may be designed to allow the subject to enter his/her age data itself in a direct manner.

In Step S9, data about body height of the subject is acquired. The control section 15 operates to indicate a sign or message for prompting to enter a body height of the subject on the display section 8, and receives an input from the numeric keypad 14. The user can simply enter data about body height of the subject using the numeric keypad 14. Instead of entry of the body height data, the apparatus 1 may be designed to have an electronic body-height meter, for example, including an electric or magnetic position sensor, and receive body height data automatically measured by the electronic body-height meter.

In Step S10, data about daily activity intensity of the subject is acquired. The control section 15 operates to indicate a sign or message for prompting to enter a daily activity intensity of the subject on the display section 8, and receives an input from the numeric keypad 14. The user can simply enter a daily activity intensity of the subject using the numeric keypad 14. The term "daily activity intensity" means numbers obtained by dividing a level of physical activity or the like in daily life into several levels in an indexed manner, and is widely known, for example, as disclosed in the Non-Patent Publication 1. If the subject is a pregnant woman, it is desirable to enter two kinds of daily activity intensity data: pre-pregnancy daily activity intensity data and pregnancy daily activity intensity data, in view of maximizing accuracy of a calculation of a pre-pregnancy energy expenditure in after-mentioned Step S193, and a calculation of a pregnancy intake energy amount in after-mentioned Step S201, because the daily activity intensity data to be entered in this Step S10 is used in these calculations. Alternatively, considering that a daily activity intensity decreases along with increase in elapsed pregnancy-period, the apparatus may be designed to prompt to enter only pre-pregnancy daily activity intensity data in this Step S10, and change (e.g. gradually reduce) the entered data depending on elapsed pregnancy-period data to be acquired in after-mentioned Step S14 so as to obtain data about current daily activity intensity of the subject. Originally, the level of daily activity intensity is not finely divided. Thus, from a practical standpoint, the necessity of strictly considering the border between a pre-pregnancy state and a pregnancy period is low.

In Step S11, data about potential difference occurring in the body of the subject due to a bioelectric impedance of the subject is acquired. Specifically, when the subject stands on the top surface of the mounting base 2 in the aforementioned Step S6, the bottom of the left feet of the subject comes into contact with the electrodes 5A, 5B, and the bottom of the right feet of the subject comes into contact with the electrodes 6A, 6B (in other words, the subject stands in such a manner as to achieve this contact state). Then, the constant AC current is supplied from the constant-current generator circuit 16 between the feet of the subject though the electrodes 5A, 6A, and thereby a potential difference corresponding to an impedance of the body of the subject occurs. This interfeet potential difference data is detected by the voltage measurement circuit 17 through the electrodes 5B, 6B. While the apparatus 1 is designed to acquire the interfeet potential difference data using the electrodes 5A, 5B, 6A, 6B in contact with respective bottoms of the right and left feet of the subject, the apparatus 1 may be designed to acquire data about potential difference between the right and left hands using electrodes in contact with the right and left palms of the subject or acquire data about potential difference between the hand and foot using electrodes in contact with the palm and foot bottom of the subject. Alternatively, the apparatus 1 may be designed to acquire about potential difference between any two body regions using electrodes attachable onto the body regions of the subject.

In Step S12, data about bioelectric impedance of the subject (hereinafter referred to occasionally as "BI data") is required. Specifically, BI data of the subject is calculated based on the Ohm's law using data about current value supplied from the constant-current generator circuit 16 to the body of the subject and the potential difference data acquired in the aforementioned Step S11. Alternatively, BI data of the subject may be calculated based on a ratio between each of the acquired potential difference data and each different known resistance of a plurality of reference registers inserted into the electric circuit in such a manner as to be in series or parallel to the body of the subject. In this case, even if the data about current value supplied to the body of the subject is unknown, BI data can be acquired.

In Step S13, it is checked whether a flag of a maternity mode is set. When the flag is set, the subject is determined to be a pregnant woman, and the process advances stepwise to after-mentioned Steps S14 to S22. Then, the process skips Step S23 and advances to Step S24. If the flag is still in a reset state, the subject is determined to be a subject other than a pregnant woman, and the process advances to Step S23 and then to Step S24. That is, the apparatus 1 is designed to determine whether a subject is a pregnant woman, based on the state of the flag to be set by the user in response to a manual operation of the status set key 13.

In Step S14, data about elapsed pregnancy-period (elapsed pregnancy-period data) of the subject determined as a pregnant woman, and data about age of the subject in a pre-pregnancy state (or pre-pregnancy age data) are acquired. The control section 15 operates to indicate a sign or message for prompting to enter an expected date of confinement of the subject on the display section 8, and receives an input from the numeric keypad 14. When the user enters an expected date of confinement of the subject, elapsed pregnancy-period data is calculated based on the entered expected date of confinement and current date data. Further, pre-pregnancy age data is calculated based on the entered expected date of confinement and birth date data. The apparatus 1 is designed to calculate the number of weeks of pregnancy (n-th week of pregnancy) and the number of days of pregnancy (n-th days of pregnancy), as the elapsed pregnancy-period data. Instead of entry of the birth date data, the apparatus 1 is designed to allow the user to enter elapsed pregnancy-period data and pre-pregnancy age data themselves in a direct manner.

In step S15, data about body weight of the subject or pregnant woman in the pre-pregnancy state (or pre-pregnancy body weight data) is acquired. The control section 15 operates to indicate a sign or message for prompting to enter a pre-pregnancy body weight of the subject on the display section 8, and receives an input from the numeric keypad 14. The user can simply enter pre-pregnancy body weight data of the subject using the numeric keypad 14. As used in this specification, the term "pre-pregnancy body weight data" does not strictly mean only a body weight value in a non-pregnant state. That is, when a body weight value in a pregnancy period is not so different from a value in a non-regnant state, i.e. the subject is in an early pregnancy period, it may be acceptable or regarded as the pre-pregnancy body weight data. Even through there is a difference among individual pregnant women or subjects, this acceptable range may include a body weight value at a time when and before the subject herself visits a doctor at a maternity clinic with suspicion of pregnancy and a diagnosis is made as pregnancy (so-called "initial visit"). In many cases, the initial visit corresponds to 8th week of pregnancy. Thus, body weight data to be entered in this Step S15 may include a body weight value approximately at or before the initial visit to a doctor at a maternity clinic, or in or before 8th week of pregnancy.

In Step S16, data about weight of a fetal region in the pregnant woman or the subject (or fetal-region weight data) is acquired. As used in this specification, the term "fetal-region weight" means a sum of a body weight of a fetus, a weight of amniotic fluid and a weight of placenta. The fetal-region weight can be estimated approximately uniquely based on the n-th week of pregnancy, as disclosed in FIG. 14 or the Patent Publication 1. Specifically, each of fetus body weight data, amniotic-fluid weight data, placenta weight data and fetal-region weight data as the sum thereof is pre-stored on the memory 18 of the apparatus 1 in association with n-th week of pregnancy, and fetal-region weight data corresponding to the n-th week of pregnancy calculated in the aforementioned Step S14 is read out in this Step S16. Alternatively, this fetal-region weight data may be calculated using a calculation formula for calculating the fetal-region weight data from the n-th week of pregnancy (function formula expressing the curve in FIG. 14).

In Step S17, various data about body composition of the subject or the pregnant woman is calculated. A process of Step S17 will be described with reference to the subroutine in FIG. 5.

Firstly, in Step S171, data about maternal weight of the subject or the pregnant woman is acquired. As used in this specification, the term "maternal weight" means a value obtained by subtracting a body weight of a fetal-region from a body weight of a pregnant woman. Thus, in this Step S171, maternal-weight data is calculated by subtracting the fetal-region weight data determined in the aforementioned Step S16 from the current body weight acquired in the aforementioned Step S6.

Then, in Step S172, data about maternal fat-percentage of the pregnant woman or the subject is acquired. As is well known, for example, as disclosed in the Patent Publication 5 or 6, a body fat percentage can be calculated based on at least body height and BI. Thus, in this Step S172, maternal fat-percentage data of the pregnant woman or the subject is calculated based on the body weight data acquired in the aforementioned Step S9, the maternal weight data acquired in the aforementioned Step S171, and the BI data acquired in the aforementioned Step S12. It is understood that the age data of the subject may be used as a correction parameter in the calculation of maternal fat-percentage data.

Then, Step S173, data about maternal fat mass of the pregnant woman or the subject (or maternal fat-mass data) is acquired. As is well known, for example, as disclosed in the Patent Publication 5 or 6, a body fat-mass can be calculated by multiplying a body weight by a body fat percentage. Thus, in this Step S173, maternal fat-mass data of the pregnant woman or the subject is calculated by the maternal weight data acquired in Step 171 by the maternal fat-percentage data acquired in the aforementioned Step S172.

Then, in Step S174, data about maternal fat-free mass of the pregnant woman or the subject (or maternal fat-free mass data) is acquired. As used in this specification, the term "fat-free mass" means a value obtained by subtracting a body fat mass from a body weight. Thus, in this step S174, maternal fat-tree mass data of the pregnant woman or the subject is calculated by subtracting the maternal fat-mass data acquired in the aforementioned Step S173 from the maternal weight data acquired in the aforementioned Step S171.

Then, in Step S175, data about maternal water mass of the pregnant woman or the subject is acquired. As with the body fat percentage, a body water mass can be calculated based on a calculation formula using at least body height and BI (Bioelectric Impedance), as a parameter. Thus, in this Step S175, maternal water mass data of the pregnant woman or the subject is calculated based on the body height data acquired in the aforementioned Step S9, the maternal weight data acquired in the aforementioned Step S171, and the BI data acquired in the aforementioned Step S12. It is understood that this maternal water mass data may be calculated by multiplying maternal fat-free mass data by 73.2%, as disclosed in the Patent Publication 5 or 6.

Then, in Step S176, data about basal metabolism of the pregnant woman or the subject (or basal metabolism data) is acquired. As disclosed in the Patent Publication 4, a basal metabolism of a pregnant woman can be calculated based on an estimation equation using at least maternal fat-free mass and age as a parameter, more preferably, an estimation equation using maternal fat-free mass, fetal-region weight, maternal weight and age as a parameter. In the apparatus 1, the following estimation equation Fbmr is pre-stored in the memory 18, and basal metabolism data is calculated by assigning to the estimation equation Fbmr the maternal fat-free mass data acquired in the aforementioned Step S174, the fetal-region weight data acquired in the aforementioned Step S16, the maternal weight data acquired in the aforementioned Step S171, and the age data acquired in the aforementioned Step S8. In the following estimation equation Fbmr, each of $A_1$, $B_1$, $C_1$, $D_1$ and $E_1$ represents a constant.

Basal metabolism=$A_1\times$(maternal fat-free mass+fetal-region weight)$^2$+$B_1\times$(maternal fat-free mass+fetal-region weight)+$C_1\times$(1/age)+$D_1\times$maternal weight+$E_1$ Returning to FIG. 4, in Step S18, various data about body composition of the pregnant woman or the subject in the pre-pregnancy state (or pre-pregnancy body composition data). A process of this Step S18 will be described with reference to the subroutine in FIG. 6.

Firstly, in Step S181, data about body-weight increment of the pregnant woman or the subject in the pregnancy period (or pregnancy body-weight increment data) is acquired. Specifically, pregnancy body-weight increment data of the subject is calculated by subtracting the pre-pregnancy body weight data acquired in the aforementioned Step S15 from the current body weight data acquired in the aforementioned Step S6.

Then, in Step S182, data about body-fat increment of the pregnant woman or the subject in the pregnancy period (or pregnancy body-fat increment data) is acquired. As disclosed in the Patent Publications 2 and 3, a difference or increment in body fat between before and after pregnancy can be calculated by multiplying an increment in body weight between before and after pregnancy by a predetermined rate. In particular, this predetermined rate is preferably about 58%. Thus, in this Step S182, pregnancy body-fat increment data of the subject is calculated by multiplying the body-weight increment data acquired in the aforementioned Step S181 by 58% (0.58).

Then, in Step S183, data about fat mass of the pregnant woman or the subject in the pre-pregnancy state (or pre-pregnancy fat mass data) is acquired. Specifically, pre-pregnancy fat mass data of the subject is calculated by subtracting the body-fat increment data acquired in the above Step S182 from the maternal fat mass data acquired in the aforementioned Step S173.

Then, in Step S184, data about fat-free mass of the pregnant woman or the subject in the pre-pregnancy state (or pre-pregnancy fat-free mass data) is calculated. Specifically, pre-pregnancy fat-free mass data of the subject is calculated by subtracting the pre-pregnancy fat mass data acquired in the above Step S183 from the pre-pregnancy body weight data acquired in the aforementioned Step S15.

Then, in Step S185, data about basal metabolism of the pregnant woman or the subject in the pre-pregnancy state (or pre-pregnancy basal metabolism data) is acquired. As disclosed in the Patent Publications 7 and 8, a basal metabolism can be calculated based on an estimation equation using at least fat-free mass and age as a parameter, more preferably, an estimation equation using fat-free mass, body weight and age as a parameter. In the apparatus 1, the following estimation equation Fbmr' is pre-stored in the memory 18, and pre-pregnancy basal metabolism data is calculated by assigning to the estimation equation Fbmr' the pre-pregnancy fat-free mass data acquired in the above Step S184, the pre-pregnancy body weight data acquired in the aforementioned Step S15 and the pre-pregnancy age data acquired in the aforementioned Step S14. In the following estimation equation Fbmr, each of $A_2$, $B_2$, $C_2$, $D_2$ and $E_2$ represents a constant.

Pre-pregnancy basal metabolism=$A_2\times$(pre-pregnancy fat-free mass)$^2$+$B_2\times$pre-pregnancy fat-free mass+$C_2\times$(1/pre-pregnancy age)+$D_2\times$pre-pregnancy body weight+$E_2$ Then, in Step S186, data about basal-metabolism increment of the pregnant woman or the subject in the pregnancy period (or basal metabolism increment data) is acquired. Specifically, basal metabolism increment data of the subject is calculated by subtracting the basal metabolism data acquired in the aforementioned Step S176 from the pre-pregnancy basal metabolism data acquired in the above Step S185.

Then, Step S187, data about body mass index of the pregnant woman or the subject in the pre-pregnancy state (or pre-pregnancy body mass index data) is acquired. A body mass index (BMI) is a value obtained by dividing a body weight by a square value of a body height. Thus, pre-pregnancy body mass index data of the subject is calculated by dividing the pre-pregnancy body weight data acquired in the aforementioned Step S15 by a square value of the body height data acquired in the aforementioned Step S9.

Returning to FIG. 4, in Step S19, an energy amount necessary for the pregnant woman or the subject in the pregnancy period or at present (pregnancy necessary energy amount) is calculated. A process of this step S19 will be described with reference to the subroutine in FIG. 7.

Firstly, in Step S191, an estimation equation Gn for calculating a pregnancy necessary energy amount of the subject is determined. As described in connection with FIG. 12, a plurality (five in this embodiment) of estimation equations Gn are prepared, respectively, for the body mass index groups, and pre-stored on the memory 18. Thus, in this Step S191, one of the estimation equations Gn prepared for the body mass index group corresponding to the pre-pregnancy body mass index data acquired in the aforementioned Step S187 is read out.

Estimation equations $G_1$ (BMI: less than 18): pre-pregnancy extra energy amount=$a_1\times(n$-th week of pregnancy$)^2$+$b_1\times n$-th week of pregnancy+$c_1$ Estimation equations $G_2$ (BMI: 18 to less than 21): pre-pregnancy extra energy amount=$a_2\times(n$-th week of pregnancy$)^2$+$b_2\times n$-th week of pregnancy+$c_2$ Estimation equations $G_3$ (BMI: 21 to less than 24):
pre-pregnancy extra energy amount=$a_3 \times$(n-th week of pregnancy)$^2 + b_3 \times$n-th week of pregnancy+$c_3$ Estimation equations $G_1$ (BMI: 24 to less than 26):
pre-pregnancy extra energy amount=$a_4 \times$(n-th week of pregnancy)$^2 + b_4 \times$n-th week of pregnancy+$c_4$ Estimation equations $G_5$ (BMI: 26 or more): pre-pregnancy extra energy amount=$a_5 \times$(n-th week of pregnancy)$^2 + b_5 \times$n-th week of pregnancy+$c_5$ Then, in Step S192, an extra energy amount for the subject in the pregnancy period (or pregnancy extra energy amount) is determined. Specifically, a pregnancy extra energy amount for the subject is calculated by assigning the elapsed pregnancy-period (n-th week of pregnancy) acquired in the aforementioned Step S14, to the estimation equations Gn read in the Step S191.

Then, in Step S193, an energy expenditure of the subject in the pre-pregnancy state (or pre-pregnancy energy expenditure) is determined. As is well known, for example, as disclosed in the Non-Patent Publication 1, an energy expenditure can be calculated by multiplying a basal metabolism by a daily activity intensity. Thus, in this Step S193, a pre-pregnancy energy expenditure of the subject is calculated by the pre-pregnancy basal metabolism acquired in the aforementioned Step S185 by the daily activity intensity data acquired in the aforementioned Step S10 (preferably, by the pre-pregnancy daily activity intensity data).

Then, in Step S194, an necessary energy amount for the pregnant woman or the subject in the pregnancy period (or pregnancy necessary energy amount) is determined by adding the pre-pregnancy energy expenditure determined the above Step S193 to the pregnancy extra energy amount determined the above Step S192.

Returning to FIG. 4, in Step S20, an energy amount which has been actually taken by the pregnant woman or the subject at the present moment in the pregnancy period (or pregnancy intake energy amount) is calculated. A process of this Step S20 will be described with reference to the subroutine in FIG. 8.

In Step S201, a pregnancy intake energy amount of the subject is determined. An intake energy amount is equivalent to an actually expended energy amount. As is well known, for example, as disclosed in the Non-Patent Publication 1, such an energy expenditure can be calculated by multiplying a basal metabolism by a daily activity intensity. Thus, in this Step S201, pregnancy intake energy amount of the subject is calculated by multiplying the basal metabolism acquired in the aforementioned Step S176 by the daily activity intensity data acquired in the aforementioned Step S10 (preferably, current daily activity intensity data).

Returning to FIG. 4, in Step S21, an excess/deficiency in energy taken by the pregnant woman or the subject (or intake-energy excess/deficiency) is calculated. Specifically, an intake-energy excess/deficiency of the subject is calculated by subtracting the pregnancy necessary energy amount determining in consideration with the physique type and the elapsed pregnancy-period of the subject in the aforementioned Step S19 from the pregnancy intake energy amount determined based on the current basal metabolism and the daily activity index of the subject in the above Step S20.

In Step S22, a comment and/or advice for healthcare to be presented to the subject is determined. Specifically, a plurality of suitable comments corresponding to respective intake energy excesses/deficiencies are pre-stored of the memory 18 of the apparatus, and one of the comments corresponding to the intake energy excess/deficiency calculated in the above Step S21 is selected.

In Step S24, the above various data acquired and determined in the apparatus 1 are output to and indicated on the display section 8 and further output to and printed by the printing section 9. FIG. 9 shows one example of a print output, wherein various data acquired according to the flowcharts in FIGS. 4 to 8 are printed out in the form of a list. When the user re-pushes down the power switch 10 or a given time has elapsed after completion of the printing, the power is turned off and the entire process is completed.

Additionally, if it is determined in Step S13 that the flag of the maternity mode is not set, a program for acquiring various biodata of a subject other than a pregnant woman will be acquired in Step S23, and the result will be output in Step S24. A data acquisition process for a subject other than a pregnant woman is well known, and deviates from the point of the present invention. Thus, its detailed description will be omitted.

The apparatus 1 may be designed, but not employed in this embodiment, to store the various acquired or calculated data on the memory 18 or an external storage device (e.g. a recording medium detachable to the apparatus 1 or a computer system incorporating a storage device) together with and in association with, for example, an identification number or code for specifying a the subject. This data accumulation technique makes it possible to refer to records about changes in each data of the subject himself/herself, and further read out one of the accumulated data which is suitable for the pre-pregnancy body weight data, in place of entry of pre-pregnancy body weight data in Step S15.

[Second Embodiment]

Figure 10:
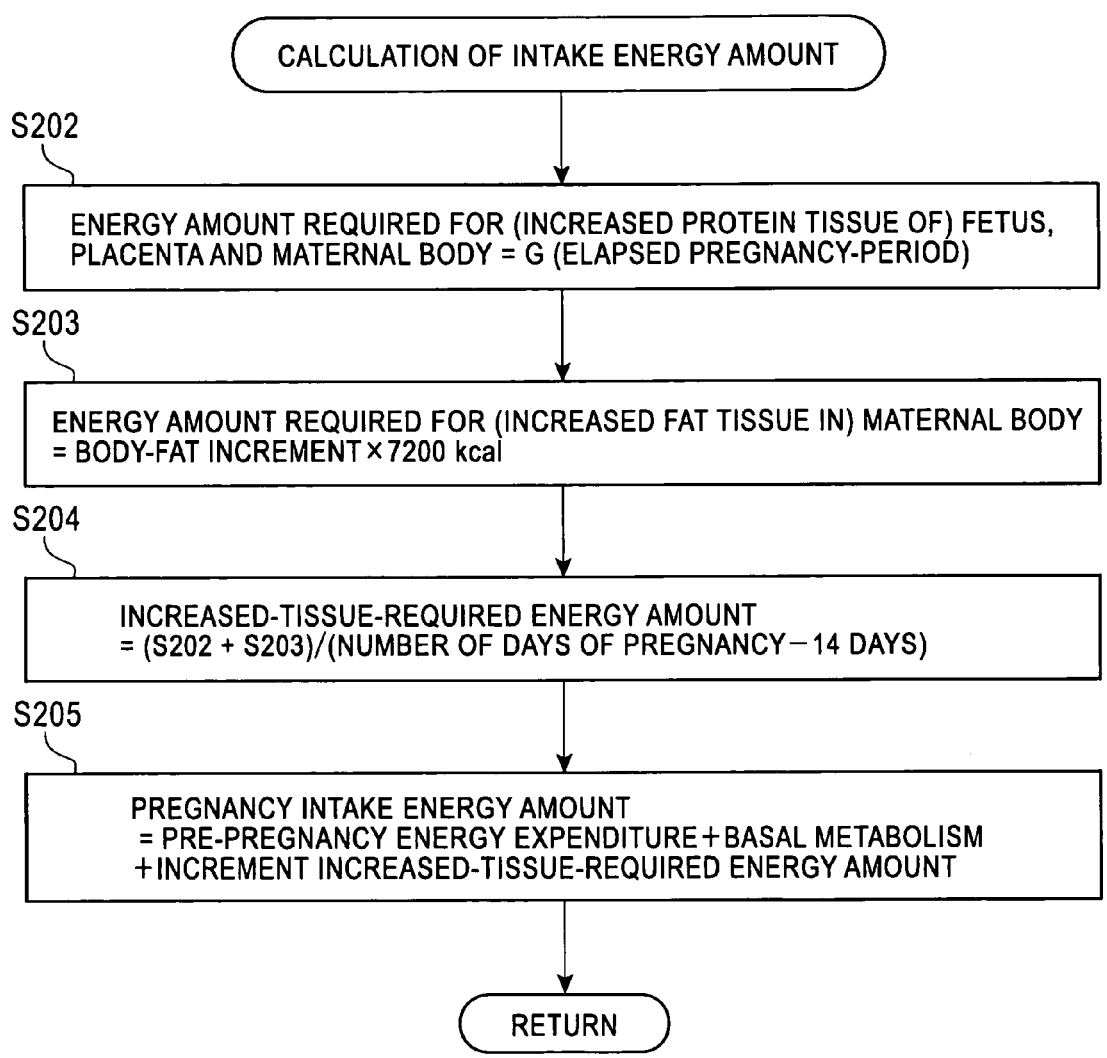
FIG. 10 is a flowchart showing a subroutine of an operation/calculation program to be executed in a biodata measurement apparatus 1 incorporating a maternity biodata measurement system according to a second embodiment of the present invention.

With reference to FIG. 10, a second embodiment of the present invention will be described. FIG. 10 is a flowchart showing a subroutine of an operation/calculation program to be executed in a biodata measurement apparatus 1 incorporating a maternity biodata measurement system according to the second embodiment. The second embodiment is primarily based on the second aspect of the present invention. Except for a process for determining a pregnancy intake energy amount in Step 20 as shown in FIG. 10, the second embodiment is substantially the same as the first embodiment. Thus, the following description will be made only for a difference between the first and second embodiments.

In the second embodiment, a calculation of pregnancy intake energy amount in Step S20 is executed according to the subroutine in FIG. 10.

Firstly, in Step S202, an energy amount required for increased protein tissue of fetus, placenta and maternal body among increased tissues of the subject due to pregnancy is estimated. As described above in connection with FIG. 13, such an energy amount can be expressed by the following estimation equation G using n-th week of pregnancy as a parameter. Thus, in this Step S202, an energy amount required for increased protein tissue of fetus, placenta and maternal body (first energy amount) is calculated by assigning to the estimation equation G the elapsed pregnancy-period (n-th week of pregnancy) acquired in the aforementioned Step S14.

Estimation equation G: energy amount=$a' \times$(n-th week of pregnancy)$^2 + b' \times$n-th week of pregnancy+$c'$ Then, in Step S203, an energy amount required for increased fat tissue in maternal body among the increased tissues of the subject due to pregnancy. As described above, an energy amount necessary for burning 1 kg of fat is about 7200 kcal. Thus, in this Step S203, an energy amount required for the fat tissue in maternal body (second energy amount) can be calculated by multiplying the body-fat increment acquired in Step S182 by the 7200 kcal.

Then, in Step S204, an increased-tissue-required energy amount of the subject or an energy amount required for increased tissues of the subject due to pregnancy is determined. This energy amount is determined by adding the first energy estimated in the above Step S202 to the second energy estimated in the above Step S203, and converting the obtained sum into a necessary energy amount per day using the elapsed pregnancy-period. While the elapsed pregnancy-period starts counting from the last menstrual day in the pre-pregnancy state, it is believed that no increase in tissue actually occurs for about 14 days between the last menstrual day and the ovulation day when it is determined whether a woman gets pregnant (fertilization). Thus, in this Step S204, an increased-tissue-required energy amount of the subject is calculated by subtracting 14 days from the elapsed pregnancy-period (the number of days of pregnancy) acquired in the aforementioned Step S14, and divided the above sum by the obtained number of days.

Then, in Step S205, an intake energy amount of the subject in the pregnancy period is determined. This pregnancy intake energy amount is calculated by adding the basal metabolism increment acquired in the aforementioned Step S186 and the increased-tissue-required energy amount determined in the aforementioned Step S204 to the pre-pregnancy energy expenditure determined in the aforementioned Step S193.

According to the process between the Steps S202 to S205, a pregnancy intake energy amount was determined for the subject who had the output illustrated in FIG. 9 as one example of the print output in the first embodiment. As the result, the pregnancy intake energy amount was 2013 kcal. In contrast, the pregnancy intake energy amount determined according to the Step S201 (FIG. 8) in the first embodiment is 1970 kcal (FIG. 9). Thus, these results obtained through the two different processes have no significant difference. However, considering that the basal metabolism increment and the increased-tissue-required energy amount are calculated separately in the second embodiment, the second embodiment can provide more accurate result even through a calculation process becomes complicated.

[Third Embodiment]

Figure 11:
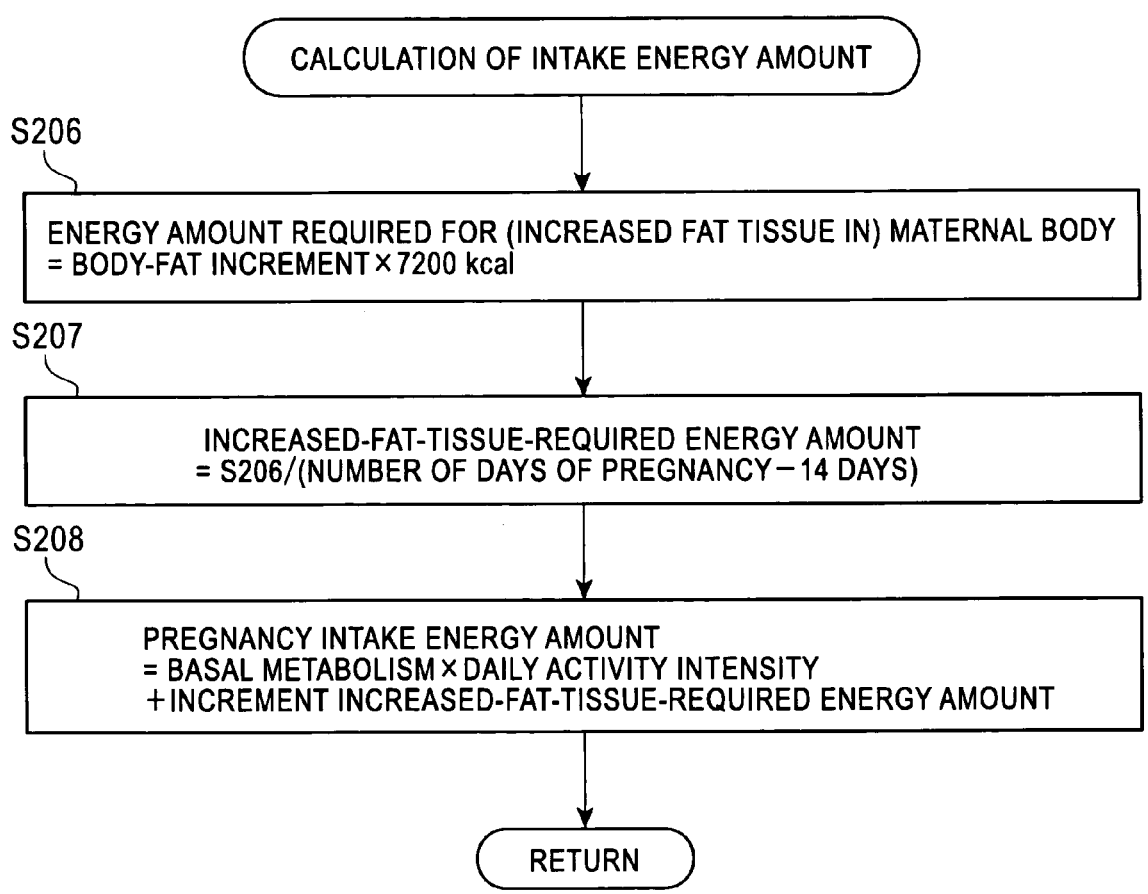
FIG. 11 is a flowchart showing a subroutine of an operation/calculation program to be executed in a biodata measurement apparatus 1 incorporating a maternity biodata measurement system according to a third embodiment of the present invention.

With reference to FIG. 11, a third embodiment of the present invention will be described. FIG. 11 is a flowchart showing a subroutine of an operation/calculation program to be executed in a biodata measurement apparatus 1 incorporating a maternity biodata measurement system according to the second embodiment. The third embodiment is primarily based on the third aspect of the present invention. Except for a process for determining a pregnancy intake energy amount in Step 20 as shown in FIG. 11, the third embodiment is substantially the same as the first embodiment. Thus, again, the following description will be made only for a difference between the first and third embodiments.

In a third embodiment of the present invention, a calculation of pregnancy intake energy amount in Step S20 is executed according to the subroutine in FIG. 11.

Firstly, in Step S206, an energy amount required for increased fat tissue in maternal body among the increased tissues of the subject due to pregnancy. As described above, an energy amount necessary for burning 1 kg of fat is about 7200 kcal. Thus, in this Step S206, an energy amount required for the fat tissue in maternal body is calculated by multiplying the body-fat increment acquired in Step S182 by the 7200 kcal.

Then, in Step S207, an increased-fat-tissue-required energy amount of the subject or an energy amount required for increased fat tissues of the subject due to pregnancy is determined. This required energy amount is determined by converting the energy amount required for the fat tissue in maternal body estimated in the above Step S206 into a necessary energy amount per day using the elapsed pregnancy-period. While the elapsed pregnancy-period starts counting from the last menstrual day in the pre-pregnancy state, it is believed that no increase in tissue actually occurs for about 14 days between the last menstrual day and the ovulation day when it is determined whether a woman gets pregnant (fertilization). Thus, in this Step S207, an increased-fat-tissue-required energy amount of the subject is calculated by subtracting 14 days from the elapsed pregnancy-period (the number of days of pregnancy) acquired in the aforementioned Step S14, and divided the above sum by the obtained number of days.

Then, in Step S208, an intake energy amount of the subject in the pregnancy period is determined. This pregnancy intake energy amount is calculated by multiplying the basal metabolism acquired in the aforementioned Step S176 by the daily activity intensity acquired in Step S10 (preferably, the current daily activity intensity), and adding the obtained value to the increased-fat-tissue-required energy amount determined in the above Step S207. That is, the increased-fat-tissue-required energy amount is added to the pregnancy intake energy amount determined in the Step S201 in the first embodiment. The pregnancy intake energy amount determined in the Step S201 is calculated using the current basal metabolism of the subject, i.e., the maternal fat-free mass, as a parameter (Step S176). Thus, it is likely that the maternal fat tissue is relatively disregarded. From this point of view, in Step S208 in the third embodiment, the increased-fat-tissue-required energy amount is added to the pregnancy intake energy amount to avoid the problem about lack of consideration for the fat tissue.

According to the process between the Steps S206 to S208, a pregnancy intake energy amount was determined for the subject who had the output illustrated in FIG. 9 as one example of the print output in the first embodiment. As the result, the pregnancy intake energy amount was 2063 kcal. While this value is largely different from 1970 kcal (FIG. 9) of pregnancy intake energy amount determined according to the Step S201 (FIG. 8) in the first embodiment, there is no significant difference from 2013 kcal of pregnancy intake energy amount determined according to the Step S205 in the second embodiment, which would have higher accuracy.

As mentioned above, the biodata measurement apparatus 1 incorporating the maternity biodata measurement system according to each of the first to third embodiments of the present invention can acquired data of a pregnant woman as a subject, particularly, data unique to each individual, such as body mass index, elapsed pregnancy-period and daily activity intensity, so as to determine a pregnancy necessary energy amount and/or a pregnancy intake energy amount.

In addition, various data to be acquired comprise data which can be readily recalled by a pregnant woman as a subject, and data, such as current body weight and bioelectric impedance, which can be measure without using a large-scale measurement device. Thus, a pregnancy necessary energy amount and/or a pregnancy intake energy amount can be determined on a individual basis in a significantly simple and easy manner.

Further, an excess/deficiency in intake energy amount can be obtained from a difference between the determined pregnancy necessary energy amount and pregnancy intake energy amount, and a suitable comment and/or advice for the obtained result can be output. This is significantly advantageous to health or nutrition management for pregnant women.

The present invention is not limited to the above specific embodiments, but various modifications and changes may be made therein without departing from the spirit and scope of the invention set forth in the appended claims. For example, the maternity biodata measurement system of the present invention may be implemented not only in an apparatus having a single housing but also in a system comprising a server computer which stores a program including basic data and an estimation equation for determining a pregnancy necessary energy amount and a pregnancy intake energy amount, a client computer capable of accessing to the server computer to enter various data, such as body mass index data, elapsed pregnancy period data and daily activity index of a subject, and a communication network for allowing the server and client computers to perform data communication therebetween.

What is claimed is:

1. A maternity biodata measurement system for measuring biodata of a pregnant woman who is a subject, comprising:
   pre-pregnancy energy-expenditure determination means for determining an energy expenditure of the subject in a pre-pregnancy state;
   pregnancy extra-energy-amount determination means for determining a suitable extra energy expenditure to be added to said pre-pregnancy energy expenditure due to pregnancy; and
   pregnancy necessary-energy-amount determination means for determining a sum of said pre-pregnancy energy expenditure and said pregnancy extra energy amount, as an energy amount necessary for the subject in a pregnancy period,
   wherein said pregnancy extra-energy-amount determination means includes:
      pre-pregnancy body-mass-index data acquisition means for acquiring data about body-mass index of the subject in the pre-pregnancy state;
      elapsed-pregnancy-period data acquisition means for acquiring data about elapsed period from the pregnancy of the subject; and
      pregnancy extra-energy-amount estimation means for estimating said pregnancy extra energy amount based on said pre-pregnancy body-mass index data and said elapsed pregnancy-period data.

2. The maternity biodata measurement system as defined in claim 1, wherein said pregnancy extra-energy-amount estimation means includes:
   estimation-equation storage means for storing a plurality of estimation equations for calculating the pregnancy extra energy amount using elapsed pregnancy-period data as a parameter, in association with pre-pregnancy body-mass index data;
   estimation-equation selection means for selecting one of said estimation equations corresponding to said acquired pre-pregnancy body-mass index data; and
   estimation-equation execution means for assigning said acquired elapsed pregnancy-period data to said selected estimation equation to calculate said pregnancy extra energy amount.

3. The maternity biodata measurement system as defined in claim 1, wherein said pre-pregnancy energy-expenditure determination means includes:
   pre-pregnancy basal-metabolism data acquisition means for acquiring data about basal metabolism of the subject in the pre-pregnancy state;
   daily-activity-intensity data acquisition means for acquiring data about daily activity intensity of the subject; and
   pre-pregnancy energy-expenditure estimation means for estimating the pre-pregnancy energy expenditure based on said pre-pregnancy basal metabolism data and said daily activity intensity data.

4. The maternity biodata measurement system as defined in claim 2, wherein said pre-pregnancy energy-expenditure determination means includes:
   pre-pregnancy basal-metabolism data acquisition means for acquiring data about basal metabolism of the subject in the pre-pregnancy state;
   daily-activity-intensity data acquisition means for acquiring data about daily activity intensity of the subject; and
   pre-pregnancy energy-expenditure estimation means for estimating the pre-pregnancy energy expenditure based on said pre-pregnancy basal metabolism data and said daily activity intensity data.

5. The maternity biodata measurement system as defined in claim 4, wherein said pre-pregnancy basal-metabolism data acquisition means includes:
   pre-pregnancy age data acquisition means for acquiring data about age of the subject in the pre-pregnancy state;
   pre-pregnancy fat-free-mass data acquisition means for acquiring data about fat-free mass of the subject in the pre-pregnancy state; and
   pre-pregnancy basal-metabolism data calculation means for calculating the pre-pregnancy basal metabolism data based on said pre-pregnancy age data and said pre-pregnancy fat-free mass data.

6. The maternity biodata measurement system as defined in claim 5, wherein said pre-pregnancy fat-free-mass data acquisition means includes:
   pre-pregnancy body-weight data acquisition means for acquiring data about body weight of the subject in the pre-pregnancy state;
   pre-pregnancy fat-mass data acquisition means for acquiring data about fat mass of the subject in the pre-pregnancy state; and
   pre-pregnancy fat-free-mass calculation means for calculating the pre-pregnancy fat-free mass data based on said pre-pregnancy body weight data and said pre-pregnancy fat mass data.

7. The maternity biodata measurement system as defined in claim 6, wherein said pre-pregnancy fat-mass data acquisition means includes:
   maternal fat-mass data acquisition means for acquiring data about maternal fat mass of the subject;
   body-fat-increment data acquisition means for acquiring data about body-fat increment of the subject in the pregnancy period; and
   pre-pregnancy fat-mass data calculation means for calculating the pre-pregnancy fat mass data based on said maternal fat mass data and said body-fat increment data.

8. The maternity biodata measurement system as defined in claim 7, wherein said maternal fat-mass data acquisition means includes:

body-weight data acquisition means for acquiring data about current body weight of the subject;

fetal-region-weight data acquisition means for acquiring data about fetal-region weight in the subject;

maternal-weight data calculation means for calculating data about maternal weight of the subject based on said current body weight data and said fetal-region weight data;

body-height data acquisition means for acquiring data about body height of the subject;

impedance data acquisition means for acquiring data about body impedance of the subject; and maternal fat-mass data calculation means for calculating the maternal fat mass data based on said maternal weight data, said body height data and said impedance data.

9. The maternity biodata measurement system as defined in claim 8, wherein said fetal-region-weight data acquisition means includes fetal-region-weight data determination means for determining the fetal-region weight data based on the elapsed pregnancy-period data acquired by said elapsed-pregnancy-period data acquisition means.

10. The maternity biodata measurement system as defined in claim 7, wherein said body-fat-increment data acquisition means includes:

body-weight-increment data acquisition means for acquiring data about body-weight increment of the subject in the pregnancy period; and body-fat-increment data determination means for determining a value obtained by multiplying said body-weight increment data by a predetermined rate, as the body-fat increment data.

11. The maternity biodata measurement system as defined in claim 9, wherein said body-fat-increment data acquisition means includes:

body-weight-increment data acquisition means for acquiring data about body-weight increment of the subject in the pregnancy period; and body-fat-increment data determination means for determining a value obtained by multiplying said body-weight increment data by a predetermined rate, as the body-fat increment data.

12. The maternity biodata measurement system as defined in claim 11, wherein said body-weight-increment data acquisition means includes:

body-weight data acquisition means for acquiring data about current body weight of the subject; and body-weight-increment data calculation means for calculating the body-weight increment data based on said current body weight data and the pre-pregnancy body weight data acquired by said pre-pregnancy body-weight data acquisition means.

13. The maternity biodata measurement system as defined in 1, which further includes:

pregnancy intake energy amount determination means for determining an energy amount which is actually taken by the subject in the pregnancy period; and intake-energy excess/deficiency data output means for outputting data about excess and deficiency in intake energy amount of the subject based on said pregnancy intake energy amount and the pregnancy necessary energy amount determined by said pregnancy necessary-energy-amount determination means.

14. The maternity biodata measurement system as defined in claim 1, which further includes:

basal-metabolism-increment determination means for determining an increment of basal metabolism of the subject in the pregnancy period;

increased-tissue-required energy-amount determination means for determining an energy amount required for increased tissue of the subject due to the pregnancy;

pregnancy intake-energy-amount determination means for determining a sum of said increment of basal metabolism, said increased-tissue-required energy amount, and the pre-pregnancy energy-expenditure determined by said pre-pregnancy energy-expenditure determination means, as an energy amount which is actually taken by the subject in the pregnancy period; and intake-energy excess/deficiency data output means for outputting data about excess and deficiency in intake energy amount of the subject based on said pregnancy intake energy amount and the pregnancy necessary energy amount determined by said pregnancy necessary-energy-amount determination means, wherein said increased-tissue-required energy-amount determination means includes:

said elapsed-pregnancy-period data acquisition means;

body-fat-increment data acquisition means for acquiring data about body-fat increment of the subject in the pregnancy period; and increased-tissue-required energy-amount estimation means for estimating the increased-tissue-required energy amount based on said elapsed pregnancy-period data and said body-fat increment data.

15. The maternity biodata measurement system as defined in claim 1, which further includes:

basal-metabolism data acquisition means for acquiring data about current basal metabolism of the subject;

daily-activity-intensity data acquisition means for acquiring data about daily activity intensity of the subject;

increased-fat-tissue-required energy-amount determination means for determining an energy amount required for increased maternal fat-tissue of the subject due to the pregnancy;

pregnancy intake-energy-amount determination means for determining an energy amount which is actually taken by the subject in the pregnancy period, based on said basal metabolism data, said daily activity intensity data, and said increased-fat-tissue-required energy amount; and intake-energy excess/deficiency data output means for outputting data about excess and deficiency in intake energy amount of the subject based on said pregnancy intake energy amount and the pregnancy necessary energy amount determined by said pregnancy necessary-energy-amount determination means, wherein said increased-fat-tissue-required energy-amount determination means includes:

said elapsed-pregnancy-period data acquisition means;

body-fat-increment data acquisition means for acquiring data about body-fat increment of the subject in the pregnancy period; and increased-tissue-required energy-amount estimation means for estimating the increased-tissue-required energy amount based on said elapsed pregnancy-period data and said body-fat increment data.

16. The maternity biodata measurement system as defined in claim 14, wherein said increased-tissue-required energy-amount estimation means includes:

first estimation-equation storage means for storing a first estimation equation for calculating first energy amount data using elapsed pregnancy-period data as a parameter;

first estimation-equation execution means for assigning said acquired elapsed pregnancy-period data to said first estimation equation to calculate said first energy amount data;

second estimation-equation storage means for storing a second estimation equation for calculating second energy amount data using body-fat increment data as a parameter;

second estimation-equation execution means for assigning said acquired body-fat increment data to said second estimation equation to calculate said second energy amount data; and increased-tissue-required energy-amount calculation means for calculating the increased-tissue-required energy amount based on said acquired elapsed pregnancy-period data and a sum of said first energy amount data and said second energy amount data.

17. The maternity biodata measurement system as defined in claim 14, wherein said body-fat-increment data acquisition means includes:

body-weight-increment data acquisition means for acquiring data about body-weight increment of the subject in the pregnancy period; and body-fat-increment data determination means for determining a value obtained by multiplying said body-weight increment data by a predetermined rate, as the body-fat increment data.

18. The maternity biodata measurement system as defined in claim 17, wherein said body-weight-increment data acquisition means includes:

body-weight data acquisition means for acquiring data about current body weight of the subject;

pre-pregnancy body-weight data acquisition means for acquiring data about body weight of the subject in the pre-pregnancy state; and body-weight-increment data calculation means for calculating the body-weight increment data based on said current body weight data and said pre-pregnancy body weight data.

19. The maternity biodata measurement system as defined in claim 14, wherein said basal-metabolism-increment determination means includes:

basal-metabolism data acquisition means for acquiring data about current basal metabolism of the subject;

pre-pregnancy basal-metabolism data acquisition means for acquiring data about basal metabolism of the subject in the pre-pregnancy state; and basal-metabolism-increment calculation means for calculating the increment of basal metabolism based on said current basal metabolism data and said pre-pregnancy basal metabolism data.

20. The maternity biodata measurement system as defined in claim 19, wherein said basal-metabolism data acquisition means includes:

age data acquisition means for acquiring data about age of the subject;

fetal-region-weight data acquisition means for acquiring data about fetal-region weight in the subject;

maternal fat-free-mass data acquisition means for acquiring data about maternal fat-free mass of the subject; and basal-metabolism calculation means for calculating the basal metabolism data based on said age data, said fetal-region weight data and said maternal fat-free mass data.

21. The maternity biodata measurement system as defined in claim 20, wherein said maternal fat-free-mass data acquisition means includes:

body-weight data acquisition means for acquiring data about current body weight of the subject;

maternal-weight data calculation means for calculating data about maternal weight of the subject based on said current body weight data and the fetal-region weight data acquired by said fetal-region-weight data acquisition means;

body-height data acquisition means for acquiring data about body height of the subject;

impedance data acquisition means for acquiring data about body impedance of the subject; and maternal fat-free-mass data calculation means for calculating the maternal fat-free mass data based on said maternal weight data, said body height data and said impedance data.

22. The maternity biodata measurement system as defined in claim 20, wherein said fetal-region-weight data acquisition means includes fetal-region-weight data determination means for determining the fetal-region weight data based on the elapsed pregnancy-period data acquired by said elapsed-pregnancy-period data acquisition means.

23. The maternity biodata measurement system as defined in claim 19, wherein said pre-pregnancy basal-metabolism data acquisition means includes:

pre-pregnancy age data acquisition means for acquiring data about age of the subject in the pre-pregnancy state;

pre-pregnancy fat-free-mass data acquisition means for acquiring data about fat-free mass of the subject in the pre-pregnancy state; and pre-pregnancy basal-metabolism data calculation means for calculating the pre-pregnancy basal metabolism data based on said pre-pregnancy age data and said pre-pregnancy fat-free mass data.

24. The maternity biodata measurement system as defined in claim 23, wherein said pre-pregnancy fat-free-mass data acquisition means includes:

pre-pregnancy body-weight data acquisition means for acquiring data about body weight of the subject in the pre-pregnancy state;

pre-pregnancy fat-mass data acquisition means for acquiring data about fat mass of the subject in the pre-pregnancy state; and pre-pregnancy fat-free-mass calculation means for calculating the pre-pregnancy fat-free mass data based on said pre-pregnancy body weight data and said pre-pregnancy fat mass data.

25. The maternity biodata measurement system as defined in claim 24, wherein said pre-pregnancy fat-mass data acquisition means includes:

maternal fat-mass data acquisition means for acquiring data about maternal fat-mass of the subject;

body-fat-increment data acquisition means for acquiring data about body-fat increment of the subject in the pregnancy period; and pre-pregnancy fat-mass-data calculation means for calculating the pre-pregnancy fat mass data based on said maternal fat mass data and said body-fat increment data.

26. The maternity biodata measurement system as defined in claim 25, wherein said maternal fat-mass data acquisition means includes:
body-weight data acquisition means for acquiring data about current body weight of the subject;
fetal-region-weight data acquisition means for acquiring data about fetal-region weight in the subject;
maternal-weight data calculation means for calculating data about maternal weight of the subject based on said current body weight data and said fetal-region weight data;
body-height data acquisition means for acquiring data about body height of the subject;
impedance data acquisition means for acquiring data about body impedance of the subject; and
maternal fat-mass data calculation means for calculating the maternal fat mass data based on said maternal weight data, said body height data and said impedance data.

27. The maternity biodata measurement system as defined in claim 26, wherein said fetal-region-weight data acquisition means includes fetal-region-weight data determination means for determining the fetal-region weight data based on the elapsed pregnancy-period data acquired by said elapsed-pregnancy-period data acquisition means.

28. The maternity biodata measurement system as defined in claim 25, wherein said body-fat-increment data acquisition means includes:
body-weight-increment data acquisition means for acquiring data about body-weight increment of the subject in the pregnancy period; and
body-fat-increment data determination means for determining a value obtained by multiplying said body-weight increment data by a predetermined rate, as the body-fat increment data.

29. The maternity biodata measurement system as defined in claim 27, wherein said body-weight-increment data acquisition means includes:
body-weight data acquisition means for acquiring data about current body weight of the subject; and
body-weight-increment data calculation means for calculating the body-weight increment data based on said current body weight data and the pre-pregnancy body weight data acquired by said pre-pregnancy body-weight data acquisition means.

30. The maternity biodata measurement system as defined in claim 14, wherein said pre-pregnancy energy-expenditure determination means includes:
pre-pregnancy basal-metabolism data acquisition means for acquiring data about basal metabolism of the subject in the pre-pregnancy state;
daily-activity-intensity data acquisition means for acquiring data about daily activity intensity of the subject; and
pre-pregnancy energy-expenditure estimation means for estimating the pre-pregnancy energy expenditure based on said pre-pregnancy basal metabolism data and said daily activity intensity data.

31. The maternity biodata measurement system as defined in claim 30, wherein said pre-pregnancy basal-metabolism data acquisition means includes:
pre-pregnancy age data acquisition means for acquiring data about age of the subject in the pre-pregnancy state;
pre-pregnancy fat-free-mass data acquisition means for acquiring data about fat-free mass of the subject in the pre-pregnancy state; and
pre-pregnancy basal-metabolism data calculation means for calculating the pre-pregnancy basal metabolism data based on said pre-pregnancy age data and said pre-pregnancy fat-free mass data.

32. The maternity biodata measurement system as defined in claim 31, wherein said pre-pregnancy fat-free-mass data acquisition means includes;
pre-pregnancy body-weight data acquisition means for acquiring data about body weight of the subject in the pre-pregnancy state;
pre-pregnancy fat-mass data acquisition means for acquiring data about fat-mass of the subject in the pre-pregnancy state; and
pre-pregnancy fat-fee-mass calculation means for calculating the pre-pregnancy fat-free mass data based on said pre-pregnancy body weight data and said pre-pregnancy fat mass data.

33. The maternity biodata measurement system as defined in claim 32, wherein said pre-pregnancy fat-mass data acquisition means includes:
maternal-fat-mass data acquisition means for acquiring data about maternal fat mass of the subject;
body-fat-increment data acquisition means for acquiring data about body-fat increment of the subject in the pregnancy period; and
pre-pregnancy fat-mass data calculation means for calculating the pre-pregnancy fat mass data based on said maternal fat mass data and said body-fat increment data.

34. The maternity biodata measurement system as defined in claim 33, wherein said maternal fat-mass data acquisition means includes:
body-weight data acquisition means for acquiring data about current body weight of the subject;
fetal-region-weight data acquisition means for acquiring data about fetal-region weight in the subject;
maternal-weight data calculation means for calculating data about maternal weight of the subject based on said current body weight data and said fetal-region weight data;
body-height data acquisition means for acquiring data about body height of the subject;
impedance data acquisition means for acquiring data about body impedance of the subject; and
maternal fat-mass data calculation means for calculating the maternal fat mass data based on said maternal weight data, said body height data and said impedance data.

35. The maternity biodata measurement system as defined in claim 34, wherein said fetal-region-weight data acquisition means includes fetal-region-weight data determination means for determining the fetal-region weight data based on the elapsed pregnancy-period data acquired by said elapsed-pregnancy-period data acquisition means.

36. The maternity biodata measurement system as defined in claim 33, wherein said body-fat-increment data acquisition means includes:
body-weight-increment data acquisition means for acquiring data about body-weight increment of the subject in the pregnancy period; and
body-fat-increment data determination means for determining a value obtained by multiplying said body-weight increment data by a predetermined rate, as the body-fat increment data.

37. The maternity biodata measurement system as defined in claim 36, wherein said body-weight-increment data acquisition means includes:

body-weight data acquisition means for acquiring data about current body weight of the subject; and body-weight-increment data calculation means for calculating the body-weight increment data based on said current body weight data and the pre-pregnancy body weight data acquired by said pre-pregnancy body-weight data acquisition means.

38. The maternity biodata measurement system as defined in claim 15, wherein said increased-fat-tissue-required energy-amount estimation means includes:

estimation-equation storage means for storing an estimation equation for calculating data about energy amount required for an increased fat tissue due to the pregnancy, using body-fat increment data as a parameter;

estimation-equation execution means for assigning said acquired body-fat increment data to said estimation equation to calculate said energy amount data required for the increased fat tissue due to the pregnancy; and increased-fat-tissue-required energy-amount calculation means for calculating the increased-fat-tissue-required energy amount based on said calculated energy amount data and said acquired elapsed pregnancy-period data.

39. The maternity biodata measurement system as defined in claim 15, wherein said body-fat-increment data acquisition means includes:

body-weight-increment data acquisition means for acquiring data about body-weight increment of the subject in the pregnancy period; and body-fat-increment data determination means for determining a value obtained by multiplying said body-weight increment data by a predetermined rate, as the body-fat increment data.

40. The maternity biodata measurement system as defined in claim 39, wherein said body-weight-increment data acquisition means includes:

body-weight data acquisition means for acquiring data about current body weight of the subject; and body-weight-increment data calculation means for calculating the body-weight increment data based on said current body weight data and pre-pregnancy body weight data.

41. The maternity biodata measurement system as defined in claim 15, wherein said basal-metabolism data acquisition means includes:

age data acquisition means for acquiring data about age of the subject;

fetal-region-weight data acquisition means for acquiring data about fetal-region weight in the subject;

maternal fat-free-mass data acquisition means for acquiring data about maternal fat-free mass of the subject; and basal-metabolism calculation means for calculating the basal metabolism data based on said age data, said fetal-region weight data and said maternal fat-free mass data.

42. The maternity biodata measurement system as defined in claim 41, wherein said maternal fat-free-mass data acquisition means includes:

body-weight data acquisition means for acquiring data about current body weight of the subject;

maternal-weight data calculation means for calculating data about maternal weight of the subject based on said current body weight data and the fetal-region weight data acquired by said fetal-region-weight data acquisition means;

body-height data acquisition means for acquiring data about body height of the subject;

impedance data acquisition means for acquiring data about body impedance of the subject; and maternal fat-free-mass data calculation means for calculating the maternal fat-free mass data based on said maternal weight data, said body height data and said impedance data.

43. The maternity biodata measurement system as defined in claim 41, wherein said fetal-region-weight data acquisition means includes fetal-region-weight data determination means for determining the fetal-region weight data based on the elapsed pregnancy-period data acquired by said elapsed-pregnancy-period data acquisition means.

* * * * *